United States Patent
Hasuoka et al.

(10) Patent No.: US 7,994,205 B2
(45) Date of Patent: Aug. 9, 2011

(54) ARYL-OR HETEROARYL-SULFONYL COMPOUNDS AS ACID SECRETION INHIBITORS

(75) Inventors: Atsushi Hasuoka, Tsukuba (JP); Terufumi Takagi, Osaka (JP); Haruyuki Nishida, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 38 days.

(21) Appl. No.: 12/225,851

(22) PCT Filed: Mar. 30, 2007

(86) PCT No.: PCT/JP2007/057102
§ 371 (c)(1), (2), (4) Date: Sep. 30, 2008

(87) PCT Pub. No.: WO2007/114338
PCT Pub. Date: Oct. 11, 2007

(65) Prior Publication Data
US 2009/0118335 A1    May 7, 2009

(30) Foreign Application Priority Data
Mar. 31, 2006 (JP) .................... 2006-100651

(51) Int. Cl.
*A01N 43/50* (2006.01)
(52) U.S. Cl. ..... 514/398; 514/407; 514/372; 548/311.1; 548/325.1; 548/186; 548/373.1; 548/377.1
(58) Field of Classification Search ............. 514/398, 514/407, 372; 548/311.1, 325.1, 373.1, 377.1, 548/186
See application file for complete search history.

(56) References Cited

U.S. PATENT DOCUMENTS

| 3,285,991 A | 11/1966 | Sellers |
| 5,910,506 A * | 6/1999 | Sugimoto et al. .............. 514/397 |
| 2004/0024014 A1 | 2/2004 | Fang et al. |
| 2008/0139639 A1 | 6/2008 | Kajino et al. |

FOREIGN PATENT DOCUMENTS

| EP | 0 295 049 | 12/1988 |
| JP | 09-048778 | 2/1997 |
| WO | WO-93/09100 | 5/1993 |
| WO | WO-97/17070 | 5/1997 |
| WO | WO-98/28269 | 7/1998 |
| WO | WO-99/42463 | 8/1999 |
| WO | WO 2004/103968 | * 12/2004 |
| WO | WO-2004/103968 | 12/2004 |
| WO | WO-2005/009389 | 2/2005 |
| WO | WO-2006/036024 | 4/2006 |

OTHER PUBLICATIONS

S. Halazy et al., "Studies on the Antitumor Agent CC-1065", *Tetrahedron Letters*, 25(14), pp. 1421-1424 (1984).
M. Artico et al., "Structure-Based Design, Synthesis, and Biological Evaluation of Novel Pyrrolyl Aryl Sulfones: HIV-1 Non-Nucleoside Reverse Transcriptase Inhibitors Active at Nanomolar Concentrations", *J. Med. Chem.*, vol. 43, pp. 1886-1891 (2000).
Supplementary European Search Report dated Oct. 27, 2010, in corresponding European Application No. 07740538.9.

* cited by examiner

*Primary Examiner* — Yong Chu
*Assistant Examiner* — Valerie Rodriguez-Garcia
(74) *Attorney, Agent, or Firm* — Edwards Angell Palmer & Dodge LLP; David G. Conlin; Mark D. Russett

(57) ABSTRACT

The present invention provides an aryl- or heteroaryl compound represented by the formula (Ia) or (Ib)

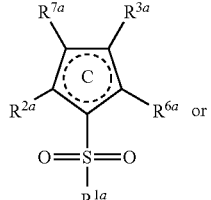

(Ia)

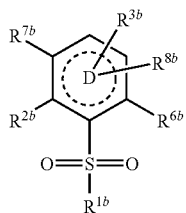

(Ib)

wherein each symbol is as defined in the specification, or a salt thereof, or a pharmaceutical composition comprising the compound and a pharmaceutically acceptable carrier. The compound has superior acid secretion inhibitory action, an antiulcer activity and the like.

4 Claims, No Drawings

ARYL- OR HETEROARYL-SULFONYL COMPOUNDS AS ACID SECRETION INHIBITORS

RELATED APPLICATIONS

This application is the 35 U.S.C. §371 national stage of PCT application no. PCT/JP2007/057102, filed Mar. 30, 2007, which claims priority to Japanese Patent Application No. 100651/2006, filed Mar. 31, 2006. The contents of these applications are incorporated herein by reference in their entirety.

TECHNICAL FIELD

The present invention relates to a compound having an acid secretion inhibitory activity.

BACKGROUND ART

Proton pump inhibitors represented by omeprazole, which suppress secretion of gastric acid for the treatment of peptic ulcer, reflux esophagitis and the like, have been widely used in clinical situations. However, the existing proton pump inhibitors are associated with problems in terms of effect and side effects. To be specific, since the existing proton pump inhibitors are unstable under acidic conditions, they are often formulated as enteric preparations, in which case several hours are required before expression of the effect. In addition, since the existing proton pump inhibitors show inconsistent treatment effects due to metabolic enzyme polymorphism and drug interaction with pharmaceutical agents such as diazepam and the like, an improvement has been desired.

As a compound having a proton pump inhibitory action, a thiazole derivative is described in patent reference 1.

As a compound having a thromboxane A2 (TXA2) antagonistic action and TXA2 synthase inhibitory action, patent reference 2 describes a compound represented by the formula

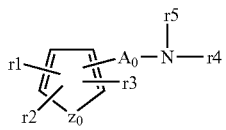

wherein r1 is carboxy, protected carboxy, carboxy(lower) alkyl, protected carboxy(lower)alkyl, carboxy(lower)alkenyl or protected carboxy(lower)alkenyl, r2 is hydrogen; lower alkyl; aminoimino or heterocyclic (lower)alkyl optionally having protected aminoimino; heterocyclic (lower)alkenyl; or heterocyclic carbonyl, r3 is hydrogen or lower alkyl, r4 is acyl, r5 is hydrogen, $A_0$ is lower alkylene, $Z_0$ is S or NH, and when r1 is carboxy or protected carboxy, then $Z_0$ is NH.

As a therapeutic drug for neoplastic diseases and autoimmune diseases, patent reference 3 describes a compound represented by the formula

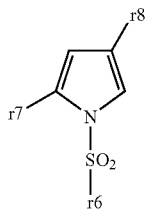

wherein r6 is aryl, aralkyl or heteroaryl, r7 is aryl or heteroaryl, and r8 is aryl, heteroaryl or optionally substituted aminomethyl.

In addition, patent reference 4 describes a pyridyl or imidazolyl derivative having a protein.isoprenyl.transferase inhibitory action.

patent reference 1: EP-A-0259085
patent reference 2: JP-A-8-119936
patent reference 3: WO2004/103968
patent reference 4: US2002/0193596

DISCLOSURE OF THE INVENTION

Problems to be Solved by the Invention

A pharmaceutical agent that effectively suppresses gastric acid secretion as known proton pump inhibitors, which is improved in instability under acidic conditions, dispersion of effects due to metabolic enzyme polymorphism and drug interaction, which are problems of known proton pump inhibitors, is expected to show more superior treatment effect on peptic ulcer, erosive esophagitis and the like. As the situation stands, however, a proton pump inhibitor capable of sufficiently satisfying these requirements has not been found. It is therefore an object of the present invention to provide a compound having a superior acid secretion suppressive effect (particularly, proton pump inhibitory action), which has been improved in these problems.

Means of Solving the Problems

The present inventors have conducted various studies and found that a compound represented by the formula (I):

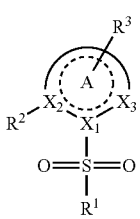

wherein ring A is a saturated or unsaturated 5- or 6-membered ring group optionally having, as a ring-constituting atom besides carbon atom, 1 to 4 hetero atoms selected from a nitrogen atom, an oxygen atom and a sulfur atom, ring-constituting atoms $X_1$ and $X_2$ are each a carbon atom or a nitrogen atom, a ring-constituting atom $X_3$ is a carbon atom, a nitrogen atom, an oxygen atom or a sulfur atom, $R^1$ is an optionally substituted aryl group or an optionally substituted heteroaryl group, $R^2$ is an optionally substituted alkyl group, an optionally substituted aryl group or an optionally substituted heteroaryl group, $R^3$ is an aminomethyl group optionally substituted by 1 or 2 lower alkyl groups, which is a substituent on a ring-constituting atom other than $X_1$, $X_2$ and $X_3$, and ring A optionally further has substituent(s) selected from a lower alkyl group, a halogen atom, a cyano group and an oxo group, excluding a compound represented by the formula

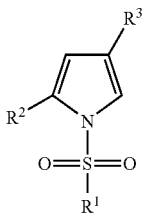

wherein each symbol is as defined above, a pyrrole ring optionally further has substituent(s) selected from a lower alkyl group, a halogen atom, a cyano group and an oxo group, or a salt thereof [hereinafter to be abbreviated as compound (I)] unexpectedly has a highly strong acid secretion inhibitory action (proton pump inhibitory action), and is sufficiently satisfactory as a pharmaceutical agent, based on which findings the present invention has been completed.

Accordingly, the present invention relates to

[1] an acid secretion inhibitor comprising a compound represented by the formula (I)

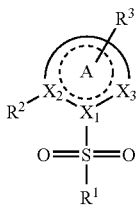

(I)

wherein ring A is a saturated or unsaturated 5- or 6-membered ring group optionally having, as a ring-constituting atom besides carbon atom, 1 to 4 hetero atoms selected from a nitrogen atom, an oxygen atom and a sulfur atom, ring-constituting atoms $X_1$ and $X_2$ are each a carbon atom or a nitrogen atom, a ring-constituting atom $X_3$ is a carbon atom, a nitrogen atom, an oxygen atom or a sulfur atom, $R^1$ is an optionally substituted aryl group or an optionally substituted heteroaryl group, $R^2$ is an optionally substituted alkyl group, an optionally substituted aryl group or an optionally substituted heteroaryl group, $R^3$ is an aminomethyl group optionally substituted by 1 or 2 lower alkyl groups, which is a substituent on a ring-constituting atom other than $X_1$, $X_2$ and $X_3$, ring A optionally further has substituent(s) selected from a lower alkyl group, a halogen atom, a cyano group and an oxo group, excluding a compound represented the formula

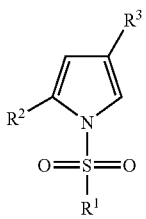

wherein each symbol is as defined above, a pyrrole ring optionally further has substituent(s) selected from a lower alkyl group, a halogen atom, a cyano group and an oxo group, or a salt thereof, or a prodrug thereof,

[2] the acid secretion inhibitor of the above-mentioned [1], wherein the compound represented by the formula (I) is a compound represented by the formula

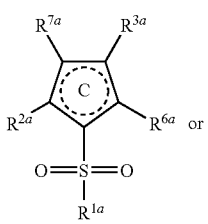

(Ia)

-continued

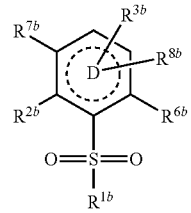

(Ib)

wherein ring C is a saturated or unsaturated 5-membered ring group optionally having, as a ring-constituting atom besides carbon atom, 1 to 4 hetero atoms selected from a nitrogen atom, an oxygen atom and a sulfur atom, ring D is a saturated or unsaturated 6-membered ring group optionally having, as a ring-constituting atom besides carbon atom, 1 to 4 hetero atoms selected from a nitrogen atom, an oxygen atom and a sulfur atom, $R^{1a}$ and $R^{1b}$ are each an optionally substituted aryl group or an optionally substituted heteroaryl group, $R^{2a}$ and $R^{2b}$ are each an optionally substituted alkyl group, an optionally substituted aryl group or an optionally substituted heteroaryl group, $R^{6a}$, $R^{7a}$, $R^{6b}$ and $R^{7b}$ are each absent, or a hydrogen atom, a lower alkyl group, a halogen atom or a cyano group, $R^{3a}$ and $R^{3b}$ are each an aminomethyl group optionally substituted by 1 or 2 lower alkyl groups, and $R^{8b}$ is absent or a hydrogen atom, a lower alkyl group, a halogen atom, a cyano group or an oxo group, excluding a compound represented by the formula

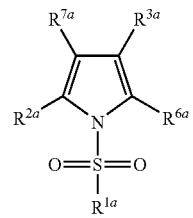

wherein each symbol is as defined above,

[3] the acid secretion inhibitor of the above-mentioned [2], wherein the compound is a compound represented by the formula (Ia),

[4] the acid secretion inhibitor of the above-mentioned [2], wherein ring C is a pyrrole ring, an imidazole ring, a thiazole ring or a pyrazole ring,

[5] the acid secretion inhibitor of the above-mentioned [2], wherein ring D is a benzene ring, a pyridine ring or a pyrimidine ring,

[6] the acid secretion inhibitor of the above-mentioned [1], which is a proton pump inhibitor,

[7] the acid secretion inhibitor of the above-mentioned [1], which is a potassium-competitive acid blocker,

[8] the acid secretion inhibitor of the above-mentioned [1], which is an agent for the prophylaxis or treatment of peptic ulcer, Zollinger-Ellison syndrome, gastritis, reflux esophagitis, symptomatic gastroesophageal reflux disease (symptomatic GERD), Barrett's esophagus, functional dyspepsia, gastric cancer, stomach MALT lymphoma or gastric hyperacidity; or an inhibitor of upper gastrointestinal hemorrhage due to peptic ulcer, acute stress ulcer, hemorrhagic gastritis or invasive stress,

[9] a compound represented by the formula

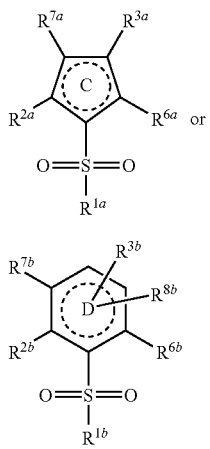

wherein ring C is a saturated or unsaturated 5-membered ring group optionally having, as a ring-constituting atom besides carbon atom, 1 to 4 hetero atoms selected from a nitrogen atom, an oxygen atom and a sulfur atom, ring D is a saturated or unsaturated 6-membered ring group optionally having, as a ring-constituting atom besides carbon atom, 1 to 4 hetero atoms selected from a nitrogen atom, an oxygen atom and a sulfur atom, $R^{1a}$ and $R^{1b}$ are each an optionally substituted aryl group or an optionally substituted heteroaryl group, $R^{2a}$ and $R^{2b}$ are each an optionally substituted alkyl group, an optionally substituted aryl group or an optionally substituted heteroaryl group, $R^{6a}$, $R^{7a}$, $R^{6b}$ and $R^{7b}$ are each absent, or a hydrogen atom, a lower alkyl group, a halogen atom or a cyano group, $R^{3a}$ and $R^{3b}$ are each an aminomethyl group optionally substituted by 1 or 2 lower alkyl groups, $R^{8b}$ is absent, or a hydrogen atom, a lower alkyl group, a halogen atom, a cyano group or an oxo group, excluding a compound represented by the formula

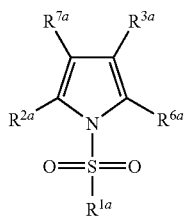

wherein each symbol is as defined above, or a salt thereof,

[10] the compound of the above-mentioned [9], which is represented by the formula (Ia-5)

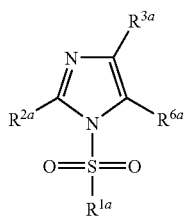

wherein $R^{1a}$ is a $C_{6-14}$ aryl group or a 5- or 6-membered aromatic heterocyclic group or a fused ring group thereof, which is optionally substituted by substituent(s) selected from (i) halogen, (ii) hydroxy, (iii) cyano, (iv) $C_{1-6}$ alkyl optionally substituted by halogen, (v) $C_{1-6}$ alkoxy optionally substituted by halogen, (vi) an amino group optionally substituted by $C_{1-6}$ alkyl, (vii) oxo, (viii) carbamoyl, (ix) mono-$C_{1-6}$ alkyl-carbamoyl, (x) di-$C_{1-6}$ alkyl-carbamoyl, (xi) $C_{1-6}$ alkylsulfonyl and (xii) $C_{1-6}$ alkyl-carbonylamino, $R^{2a}$ is an optionally substituted alkyl group, an optionally substituted aryl group or an optionally substituted heteroaryl group, $R^{3a}$ is an aminomethyl group optionally substituted by 1 or 2 lower alkyl groups, and $R^{6a}$ is a hydrogen atom, a lower alkyl group, a halogen atom or a cyano group,

[11] a prodrug of the compound of the above-mentioned [9],

[12] a pharmaceutical agent comprising the compound of the above-mentioned [9] or a prodrug thereof,

[13] a method of treating or preventing peptic ulcer, Zollinger-Ellison syndrome, gastritis, reflux esophagitis, symptomatic gastroesophageal reflux disease (symptomatic GERD), Barrett's esophagus, functional dyspepsia, gastric cancer, stomach MALT lymphoma or gastric hyperacidity; or a method of inhibiting upper gastrointestinal hemorrhage due to peptic ulcer, acute stress ulcer, hemorrhagic gastritis or invasive stress, which comprises administering an effective amount of the compound of the above-mentioned [9] or a prodrug thereof to a mammal, and

[14] use of the compound of the above-mentioned [9] or a prodrug thereof for the production of an agent for the prophylaxis or treatment of peptic ulcer, Zollinger-Ellison syndrome, gastritis, reflux esophagitis, symptomatic gastroesophageal reflux disease (symptomatic GERD), Barrett's esophagus, functional dyspepsia, gastric cancer, stomach MALT lymphoma or gastric hyperacidity; or an inhibitor of upper gastrointestinal hemorrhage due to peptic ulcer, acute stress ulcer, hemorrhagic gastritis or invasive stress.

In addition, the present invention relates to

[15] a proton pump inhibitor comprising a compound represented by the formula (I)

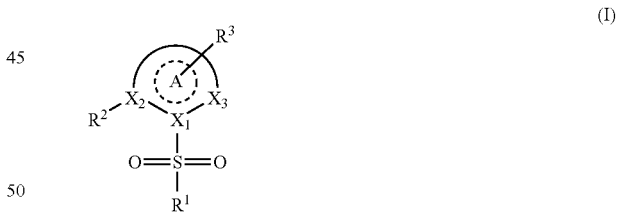

wherein ring A is a saturated or unsaturated 5- or 6-membered ring group optionally having, as a ring-constituting atom besides carbon atom, 1 to 4 hetero atoms selected from a nitrogen atom, an oxygen atom and a sulfur atom, ring-constituting atoms $X_1$ and $X_2$ are each a carbon atom or a nitrogen atom, a ring-constituting atom $X_3$ is a carbon atom, a nitrogen atom, an oxygen atom or a sulfur atom, $R^1$ is an optionally substituted aryl group or an optionally substituted heteroaryl group, $R^2$ is an optionally substituted alkyl group, an optionally substituted aryl group or an optionally substituted heteroaryl group, $R^3$ is an aminomethyl group optionally substituted by 1 or 2 lower alkyl groups, which is a substituent on a ring-constituting atom other than $X_1$, $X_2$ and $X_3$, ring A optionally further has substituent(s) selected from a lower alkyl group, a halogen atom, a cyano group and an oxo group, excluding a compound represented by the formula

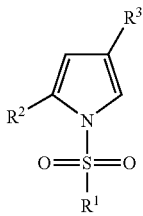

wherein each symbol is as defined above, and a pyrrole ring optionally further has substituent(s) selected from a lower alkyl group, a halogen atom, a cyano group and an oxo group, or a salt thereof, or a prodrug thereof,

[16] the inhibitor of the above-mentioned [15], wherein the compound represented by the formula (I) is a compound represented by the formula

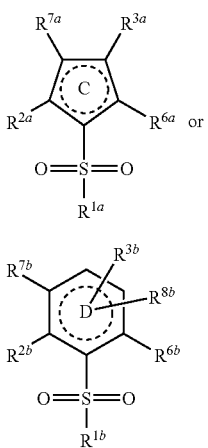

wherein ring C is a saturated or unsaturated 5-membered ring group optionally having, as a ring-constituting atom besides carbon atom, 1 to 4 hetero atoms selected from a nitrogen atom, an oxygen atom and a sulfur atom, ring D is a saturated or unsaturated 6-membered ring group optionally having, as a ring-constituting atom besides carbon atom, 1 to 4 hetero atoms selected from a nitrogen atom, an oxygen atom and a sulfur atom, $R^{1a}$ and $R^{1b}$ are each an optionally substituted aryl group or an optionally substituted heteroaryl group, $R^{2a}$ and $R^{2b}$ are each an optionally substituted alkyl group, an optionally substituted aryl group or an optionally substituted heteroaryl group, $R^{6a}$, $R^{7a}$, $R^{6b}$ and $R^{7b}$ are each absent, or a hydrogen atom, a lower alkyl group, a halogen atom or a cyano group, $R^{3a}$ and $R^{3b}$ are each an aminomethyl group optionally substituted by 1 or 2 lower alkyl groups, and $R^{8b}$ is absent, or a hydrogen atom, a lower alkyl group, a halogen atom, a cyano group or an oxo group, excluding a compound represented by the formula

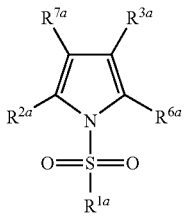

wherein each symbol is as defined above,

[17] the inhibitor of the above-mentioned [16], wherein the compound is a compound represented by the formula (Ia),

[18] the inhibitor of the above-mentioned [16], wherein ring C is a pyrrole ring, an imidazole ring or a thiazole ring,

[19] the inhibitor of the above-mentioned [16], wherein ring D is a benzene ring, a pyridine ring or a pyrimidine ring,

[20] an agent for the treatment or prophylaxis of peptic ulcer, Zollinger-Ellison syndrome, gastritis, reflux esophagitis, Symptomatic Gastroesophageal Reflux Disease (Symptomatic GERD), NUD (Non Ulcer Dyspepsia), gastric cancer, stomach MALT lymphoma, ulcer caused by a non-steroidal anti-inflammatory agent or hyperacidity or ulcer due to postoperative stress; or an inhibitor of upper gastrointestinal hemorrhage due to peptic ulcer, acute stress ulcer, hemorrhagic gastritis or invasive stress, comprising a proton pump inhibitor of the above-mentioned [15],

[21] a compound represented by the formula

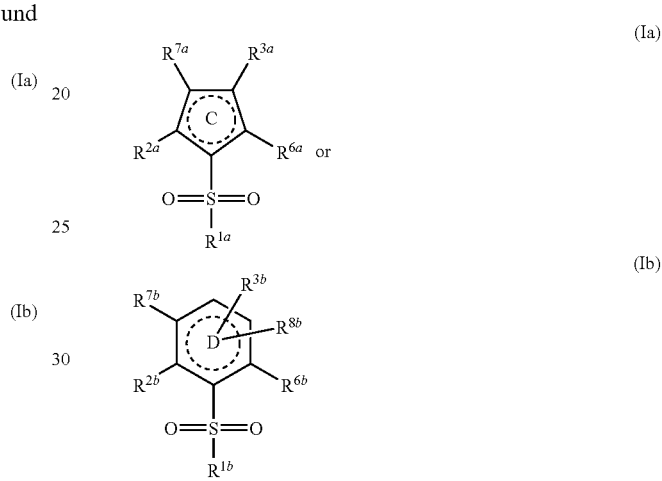

wherein ring C is a saturated or unsaturated 5-membered ring group optionally having, as a ring-constituting atom besides carbon atom, 1 to 4 hetero atoms selected from a nitrogen atom, an oxygen atom and a sulfur atom, ring D is a saturated or unsaturated 6-membered ring group optionally having, as a ring-constituting atom besides carbon atom, 1 to 4 hetero atoms selected from a nitrogen atom, an oxygen atom and a sulfur atom, $R^{1a}$ and $R^{1b}$ are each an optionally substituted aryl group or an optionally substituted heteroaryl group, $R^{2a}$ and $R^{2b}$ are each an optionally substituted alkyl group, an optionally substituted aryl group or an optionally substituted heteroaryl group, $R^{6a}$, $R^{7a}$, $R^{6b}$ and $R^{7b}$ are each absent, or a hydrogen atom, a lower alkyl group, a halogen atom or a cyano group, $R^{3a}$ and $R^{3b}$ are each an aminomethyl group optionally substituted by 1 or 2 lower alkyl groups, and $R^{8b}$ is absent, or a hydrogen atom, a lower alkyl group, a halogen atom, a cyano group or an oxo group, excluding a compound represented by the formula

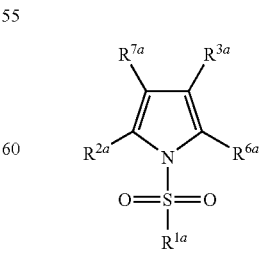

wherein each symbol is as defined above, or a salt thereof,

[22] a prodrug of the compound of the above-mentioned [21],

[23] a pharmaceutical agent comprising the compound of the above-mentioned [21] or a prodrug thereof,

[24] a pharmaceutical agent of the above-mentioned [23], which is an agent for the prophylaxis or treatment of peptic ulcer, Zollinger-Ellison syndrome, gastritis, reflux esophagitis, symptomatic gastroesophageal reflux disease (symptomatic GERD), NUD (Non Ulcer Dyspepsia), gastric cancer, stomach MALT lymphoma, ulcer caused by non-steroidal anti-inflammatory agent or gastric hyperacidity or ulcer due to postoperative stress; or an inhibitor of upper gastrointestinal hemorrhage due to peptic ulcer, acute stress ulcer, hemorrhagic gastritis or invasive stress,

[25] a method for the prophylaxis or treatment of peptic ulcer, Zollinger-Ellison syndrome, gastritis, reflux esophagitis, symptomatic gastroesophageal reflux disease (symptomatic GERD), NUD (Non Ulcer Dyspepsia), gastric cancer, stomach MALT lymphoma, ulcer caused by non-steroidal anti-inflammatory agent or gastric hyperacidity or ulcer due to postoperative stress; or a method of inhibiting upper gastrointestinal hemorrhage due to peptic ulcer, acute stress ulcer, hemorrhagic gastritis or invasive stress, comprising administering an effective amount of the compound of the above-mentioned [21] or a prodrug thereof to mammal, and

[26] use of the compound of the above-mentioned [21] or a prodrug thereof for the production of an agent for the prophylaxis or treatment of peptic ulcer, Zollinger-Ellison syndrome, gastritis, reflux esophagitis, symptomatic gastroesophageal reflux disease (symptomatic GERD), NUD (Non Ulcer Dyspepsia), gastric cancer, stomach MALT lymphoma, ulcer caused by non-steroidal anti-inflammatory agent or gastric hyperacidity or ulcer due to postoperative stress; or an inhibitor of upper gastrointestinal hemorrhage due to peptic ulcer, acute stress ulcer, hemorrhagic gastritis or invasive stress.

EFFECT OF THE INVENTION

Compound (I) shows a superior proton pump inhibitory action. Conventional proton pump inhibitors such as omeprazole, lansoprazole and the like form a covalent bond with a cysteine residue of $H^+/K^+$-ATPase, and irreversibly inhibit the enzyme activity. In contrast, compound (I) inhibits proton pump ($H^+/K^+$-ATPase) activity in a reversible and $K^+$ antagonist-like inhibitory manner, and consequently suppresses acid secretion. Therefore, it is sometimes called a potassium-competitive acid blocker (P-CAB), or an acid pump antagonist (APA). Compound (I) rapidly expresses the action and shows the maximum efficacy from the initial administration. Furthermore, it characteristically shows less influence of metabolic polymorphism (variation between patients) and long duration of action. Accordingly, the present invention can provide a clinically useful agent for the prophylaxis or treatment of peptic ulcer (e.g., gastric ulcer, duodenal ulcer, anastomotic ulcer, ulcer caused by non-steroidal anti-inflammatory agent, ulcer due to postoperative stress etc.), Zollinger-Ellison syndrome, gastritis, erosive esophagitis, reflux esophagitis, symptomatic gastroesophageal reflux disease (Symptomatic GERD), Barrett's esophagus, functional dyspepsia including NUD (Non Ulcer Dyspepsia), gastric cancer, stomach MALT lymphoma or hyperacidity; or a suppressant of upper gastrointestinal hemorrhage due to peptic ulcer, acute stress ulcer, hemorrhagic gastritis or invasive stress; and the like. Since compound (I) shows low toxicity and is superior in water-solubility, in vivo kinetics and efficacy expression, it is useful as a pharmaceutical composition. Furthermore, since compound (I) is stable even under acidic conditions, it can be administered orally as a conventional tablet and the like without formulating into an enteric-coated preparation. This has an advantageous consequence that the preparation (tablet and the like) can be made smaller, and can be easily swallowed by patients having difficulty in swallowing, particularly the elderly and children. In addition, since it is free of a sustained release effect afforded by enteric-coated preparations, a gastric acid secretion-suppressive action is expressed rapidly, and symptoms such as pain and the like can be alleviated rapidly.

In the formula (I), ring A is a saturated or unsaturated 5- or 6-membered ring group optionally having, as a ring-constituting atom besides carbon atom, 1 to 4 hetero atoms selected from a nitrogen atom, an oxygen atom and a sulfur atom. Specific examples of ring A include 5-membered ring groups such as a thiophene ring, a furan ring, a pyrrole ring, an imidazole ring, a pyrazole ring, an isothiazole ring, a thiazole ring, an isoxazole ring, an oxazole ring, a pyrrolidine ring, a pyrroline ring, an imidazolidine ring, an imidazoline ring, a pyrazolidine ring, a pyrazoline ring, a furazan ring, an oxadiazole ring (e.g., 1,2,3-oxadiazole ring, 1,2,4-oxadiazole ring, 1,3,4-oxadiazole ring), a thiadiazole ring (e.g., 1,2,3-thiadiazole ring, 1,2,4-thiadiazole ring, 1,3,4-thiadiazole ring), a triazole ring (e.g., 1,2,3-triazole ring, 1,2,4-triazole ring), a tetrazole ring, a tetrahydrofuran ring, a cyclopentane ring, a cyclopentene ring, a cyclopentadiene ring and the like; and 6-membered ring groups such as a pyridine ring, a pyrazine ring, a pyrimidine ring, a pyridazine ring, a piperidine ring, a piperazine ring, a morpholine ring, a thiomorpholine ring, a pyran ring, a thiopyran ring, a triazine ring (e.g., 1,2,4-triazine ring, 1,3,5-triazine ring), an oxazine ring (e.g., 1,4-oxazine ring, 1,3-oxazine ring), a thiazine ring (e.g., 1,4-thiazine ring, 1,3-thiazine ring), an oxadiazine ring, a thiadiazine ring, a tetrahydropyran ring, a tetrahydropyridine ring (e.g., 1,2,3,6-tetrahydropyridine ring), a dihydropyridine ring (e.g., 1,4-dihydropyridine ring), a cyclohexane ring, a cyclohexene ring, a cyclohexadiene ring, a benzene ring and the like.

Here, the ring-constituting atom ($X_1$) of ring A, to which a group represented by $-SO_2-R^1$ is bonded and the ring-constituting atom ($X_2$) of ring A, to which a substituent represented by $R^2$ is bonded is a carbon atom or a nitrogen atom.

The ring-constituting atom ($X_3$) adjacent to $X_1$ is a carbon atom, a nitrogen atom, an oxygen atom or a sulfur atom. When $X_3$ is a carbon atom or a nitrogen atom, a substituent ($R^6$) selected from a lower alkyl group, a halogen atom and a cyano group may be present at $X_3$. Examples of the "lower alkyl group" for $R^6$ include a $C_{1-4}$ alkyl group such as methyl, ethyl, propyl, isopropyl, butyl, isobutyl, sec-butyl, tert-butyl etc. and the like.

Examples of the "halogen atom" for $R^6$ include a fluorine atom, a chlorine atom, a bromine atom and an iodine atom.

Examples of the aryl group in the "optionally substituted aryl group" for $R^1$ include a $C_{6-14}$ aryl group such as phenyl, 1-naphthyl, 2-naphthyl, 2-biphenylyl, 3-biphenylyl, 4-biphenylyl, 2-anthryl and the like.

Examples of the substituent of the aryl group include (1) a halogen atom (e.g., fluorine atom, chlorine atom, bromine atom, iodine atom etc.), (2) nitro, (3) cyano, (4) hydroxy, (5) $C_{1-6}$ alkoxy optionally having 1 to 5 (preferably 1 to 3) halogen atoms (e.g., fluorine, chlorine, bromine, iodine) (e.g., methoxy, ethoxy, propoxy, isopropoxy, butoxy, isobutoxy, sec-butoxy, pentyloxy, hexyloxy, fluoromethoxy etc.), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio optionally having 1 to 5 (preferably 1 to 3) halogen atoms (e.g., fluorine, chlorine, bromine, iodine) (e.g., methylthio, difluoromethylthio, trifluoromethylthio, ethylthio, propylthio, isopropylthio, butylthio, 4,4,4-trifluorobutylthio, pentylthio, hexylthio etc.), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atom, 1 or 2 kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.), (50) a $C_{1-6}$ alkyl group optionally having 1 to 5 (preferably 1 to 3) halogen atoms (e.g., fluorine, chlorine, bromine, iodine) (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl etc.), (51) a $C_{2-6}$ alkenyl group (e.g., allyl, isopropenyl, isobutenyl, 1-methylallyl, 2-pentenyl, 2-hexenyl etc.) optionally having 1 to (preferably 1 to 3) halogen atoms (e.g., fluorine, chlorine, bromine, iodine), (52) a $C_{2-6}$ alkynyl group (e.g., propargyl, 2-butynyl, 3-butynyl, 3-pentynyl, 3-hexynyl etc.), (53) a $C_{6-14}$ aryl group (e.g., phenyl etc.) optionally having 1 to 5 (preferably 1 to 3) halogen atoms (e.g., fluorine, chlorine, bromine, iodine), (54) $C_{7-16}$ aralkyl (e.g., benzyl, phenethyl etc.) optionally having 1 to 5 (preferably 1 to 3) halogen atoms (e.g., fluorine, chlorine, bromine, iodine), (55) oxo, and the like.

The substituent may be present at a substitutable position, and the number of the substituents is 1 to 5, preferably 1 to 3.

Examples of the heteroaryl group in the "optionally substituted heteroaryl group" for $R^1$ include a 5- or 6-membered aromatic heterocyclic group or a fused ring group thereof such as pyrrolyl (e.g., 1-, 2- or 3-pyrrolyl), pyrazolyl (e.g., 1-, 3-, 4- or 5-pyrazolyl), imidazolyl (e.g., 1-, 2-, 4- or 5-imidazolyl), triazolyl (e.g., 1,2,3-triazol-4-yl, 1,2,3-triazol-1-yl, 1,2,3-triazol-5-yl, 1,2,4-triazol-1-yl, 1,2,4-triazol-3-yl, 1,2, 4-triazol-4-yl, 1,2,4-triazol-5-yl), tetrazolyl (e.g., tetrazol-1-, 2- or 5-yl), furyl (e.g., 2- or 3-furyl), thienyl (e.g., 2- or 3-thienyl), oxazolyl (e.g., 2-, 4- or 5-oxazolyl), isoxazolyl (e.g., 3-, 4- or 5-isoxazolyl), oxadiazolyl (e.g., 1,2,3-oxadiazol-4- or 5-yl, 1,2,4-oxadiazol-3- or 5-yl, 1,2,5-oxadiazol-3-yl, 1,3,4-oxadiazol-2-yl), thiazolyl (e.g., 2-, 4- or 5-thiazolyl), isothiazolyl (e.g., 3-, 4- or 5-isothiazolyl), thiadiazolyl (e.g., 1,2,3-thiadiazol-4- or 5-yl, 1,2,4-thiadiazol-3- or 5-yl, 1,2,5-thiadiazol-3-yl, 1,3,4-thiadiazol-2-yl), pyridyl (e.g., 2-, 3- or 4-pyridyl), pyridazinyl (e.g., 3- or 4-pyridazinyl), pyrimidinyl (e.g., 2-, 4- or 5-pyrimidinyl), pyrazinyl, benzofuryl (e.g., 2- or 3-benzofuryl), benzothienyl (e.g., 2- or 3-benzothienyl), isoindolyl (e.g., 1- or 3-isoindolyl), benzimidazolyl (e.g., 2-benzimidazolyl), benzoxazolyl (e.g., 2-benzoxazolyl), benzisoxazolyl (e.g., 3-benzisoxazolyl), benzothiazolyl (e.g., 2-benzothiazolyl), benzisothiazolyl (e.g., 3-benzisothiazolyl), cinnolinyl (e.g., 3- or 4-cinnolinyl), quinazolinyl (e.g., 2- or 4-quinazolinyl), quinoxalinyl (e.g., 2- or 3-quinoxalinyl), phthalazinyl (e.g., 1- or 4-phthalazinyl), pteridinyl, indolyl (e.g., 3H-indol-2-, 3-, 4-, 5-, 6- or 7-yl), quinolyl (e.g., 3-, 4-, 5-, 6-, 7- or 8-quinolyl), isoquinolyl (e.g., 1-, 3- or 4-isoquinolyl), pyrido[2,3-d]pyrimidinyl (e.g., pyrido[2,3-d]pyrimidin-2-yl), naphthyridinyl such as 1,5-, 1,6-, 1,7-, 1,8-, 2,6- or 2,7-naphthyridinyl and the like (e.g., 1,5-naphthyridin-2- or 3-yl), thieno[2,3-d]pyridyl (e.g., thieno[2,3-d]pyridin-3-yl), pyrazinoquinolyl (e.g., pyrazino[2,3-d]quinolin-2-yl), imidazo[1,2-a]pyridyl, imidazo[2,1-b]thiazolyl, imidazo[1,2-a]pyrimidinyl, imidazo[1,2-b]pyridazinyl, imidazo[1,2-a]imidazolyl, imidazo[2,1-b](1.3.4)thiadiazolyl, pyrazolo[1,5-a]pyrimidinyl, pyrazolo[5,1-b]thiazolyl or pyrazolo[1,5-a]pyridyl and the like.

Examples of the substituent of the heteroaryl group include those similar to the substituents which the aforementioned aryl group in $R^1$ optionally has. The substituent may be present at a substitutable position, and the number of the substituents is 1 to 5, preferably 1 to 3.

Examples of the alkyl group of the "optionally substituted alkyl group" for $R^2$ include a $C_{1-6}$ alkyl group such as methyl, ethyl, n-propyl, isopropyl, n-butyl, isobutyl, sec-butyl, tert-butyl, n-pentyl, sec-pentyl, isopentyl, neopentyl, n-hexyl, isohexyl and the like.

Examples of the substituent of the alkyl group include (1) a halogen atom (e.g., fluorine atom, chlorine atom, bromine atom, iodine atom etc.), (2) nitro, (3) cyano, (4) hydroxy, (5) $C_{1-6}$ alkoxy optionally having 1 to 3 halogen atoms (e.g., fluorine, chlorine, bromine, iodine) (e.g., methoxy, ethoxy, propoxy, isopropoxy, butoxy, isobutoxy, sec-butoxy, pentyloxy, hexyloxy, fluoromethoxy etc.), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio optionally having 1 to 3 halogen atoms (e.g., fluorine, chlorine, bromine, iodine) (e.g., methylthio, difluoromethylthio, trifluoromethylthio, ethylthio, propylthio, isopropylthio, butylthio, 4,4,4-trifluorobutylthio, pentylthio, hexylthio etc.), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.) (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) a 5- to 7-membered saturated cyclic amino optionally containing, besides one nitrogen atom and carbon atom, 1 or 2 kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atom, 1 or 2 kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.) and the like.

The number of the substituents is 1 to 3.

Examples of the "optionally substituted aryl group" or "optionally substituted heteroaryl group" for $R^2$ include those similar to the aforementioned "optionally substituted aryl group" and "optionally substituted heteroaryl group" for $R^1$.

$R^3$ is a substituent on a ring-constituting atom other than $X_1$, $X_2$ and $X_3$, and is an aminomethyl group optionally substituted by 1 or 2 lower alkyl groups (—$CH_2$—$NR^4R^5$).

Examples of the lower alkyl group of the "aminomethyl group optionally substituted by 1 or 2 lower alkyl groups" include a $C_{1-4}$ alkyl group such as methyl, ethyl, propyl, isopropyl, butyl, isobutyl, sec-butyl, tert-butyl etc. and the like.

That is, $R^4$ and $R^5$ in —$CH_2$—$NR^4R^5$ for $R^3$ are the same or different and each is a hydrogen atom or a lower alkyl group such as a $C_{1-4}$ alkyl group and the like.

Preferred as $R^3$ is, from those mentioned above, an aminomethyl group (—$CH_2$—$NH_2$), a methylaminomethyl group (—$CH_2$—$NH(CH_3)$) and a dimethylaminomethyl group (—$CH_2$—$N(CH_3)_2$).

Ring A may further have substituent(s), besides the substituent represented by —$SO_2$—$R^1$, $R^2$ and $R^3$, at substitutable position(s). Preferred as the substituent are a lower alkyl group (e.g., $C_{1-4}$ alkyl group such as methyl, ethyl, propyl, isopropyl, butyl, isobutyl, sec-butyl, tert-butyl etc. and the like), a halogen atom (e.g., fluorine atom, chlorine atom, bromine atom, iodine atom), a cyano group and an oxo group. The number of the substituents is 1 to 3, preferably 1 or 2.

A compound represented by the formula (I) is specifically a compound represented by the formula (I')

wherein ring B is a saturated or unsaturated 5- or 6-membered ring group optionally having, as a ring-constituting atom besides carbon atom, 1 to 4 hetero atoms selected from a nitrogen atom, an oxygen atom and a sulfur atom, ring-constituting atoms $X_1$ and $X_2$ are each a carbon atom or a nitrogen atom, ring-constituting atoms $X_3$ and $X_4$ are each a carbon atom, a nitrogen atom, an oxygen atom or a sulfur atom, when $X_3$ or $X_4$ is a carbon atom or a nitrogen atom, each may have substituent(s) selected from a lower alkyl group, a halogen atom and a cyano group, $X_5$ is (1) a carbon atom or a nitrogen atom, said carbon atom or nitrogen atom having substituent $R^3$ thereon, or (2) —$X_6$—$X_7$— (wherein $X_6$ and $X_7$ are each a carbon atom, a nitrogen atom, an oxygen atom or a sulfur atom, at least one of $X_6$ and $X_7$ is a carbon atom or a nitrogen atom, having a substituent $R^3$ on its atom, and the other is any of a carbon atom, a nitrogen atom, an oxygen atom and a sulfur atom, when it is a carbon atom or a nitrogen atom, it may have a substituent ($R^8$) selected from a lower alkyl group, a halogen atom and a cyano group, and when it is a carbon atom, it is optionally substituted by oxo), $R^1$ is an optionally substituted aryl group or an optionally substituted heteroaryl group, $R^2$ is an optionally substituted alkyl group, an optionally substituted aryl group or an optionally substituted heteroaryl group, and $R^3$ is aminomethyl ($-CH_2-NR^4R^5$) group ($R^4$ and $R^5$ are the same or different and each is a hydrogen atom or a lower alkyl group such as a $C_{1-4}$ alkyl group (e.g., methyl, ethyl) and the like) optionally substituted by 1 or 2 lower alkyl groups, excluding a compound represented by the formula

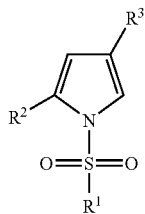

wherein each symbol is as defined above, and a pyrrole ring is optionally further substituted by a substituent selected from a lower alkyl group, a halogen atom and a cyano group, or a salt thereof [hereinafter to be abbreviated as compound (I')].

In compound (I'), examples of the "saturated or unsaturated 5- or 6-membered ring group optionally having, as a ring-constituting atom besides carbon atom, 1 to 4 hetero atoms selected from a nitrogen atom, an oxygen atom and a sulfur atom" for ring B include those similar to the 5- or 6-membered ring groups exemplified for ring A.

The ring-constituting atoms $X_1$ and $X_2$ are each a carbon atom or a nitrogen atom, and the ring-constituting atoms $X_3$ and $X_4$ are each a carbon atom, a nitrogen atom, an oxygen atom or a sulfur atom.

When $X_3$ is a carbon atom or a nitrogen atom, a substituent ($R^6$) selected from a lower alkyl group, a halogen atom and a cyano group may be present on $X_3$.

Specific examples of $R^6$ include those similar to those exemplified for the aforementioned compound (I).

When $X_4$ is a carbon atom or a nitrogen atom, a substituent ($R^7$) selected from a lower alkyl group, a halogen atom and a cyano group may be present on $X_4$.

Specific examples of the "lower alkyl group" and "halogen atom" for $R^7$ include those similar to $R^6$.

In addition, specific examples of the above-mentioned "lower alkyl group" and "halogen atom" for $R^8$ include those similar to $R^6$.

In compound (I'), examples of the $R^1$, $R^2$ and $R^3$ include those similar to those exemplified for $R^1$, $R^2$ and $R^3$ of compound (I).

Preferable embodiments of compounds (I) and (I') are the following compounds (Ia) and (Ib).

A compound represented by the formula

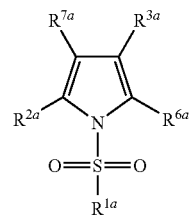 or

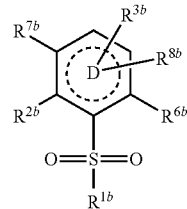

wherein ring C is a saturated or unsaturated 5-membered ring group optionally having, as a ring-constituting atom besides carbon atom, 1 to 4 hetero atoms selected from a nitrogen atom, an oxygen atom and a sulfur atom, ring D is a saturated or unsaturated 6-membered ring group optionally having, as a ring-constituting atom besides carbon atom, 1 to 4 hetero atoms selected from a nitrogen atom, an oxygen atom and a sulfur atom, $R^{1a}$ and $R^{1b}$ are each an optionally substituted aryl group or an optionally substituted heteroaryl group, $R^{2a}$ and $R^{2b}$ are each an optionally substituted alkyl group, an optionally substituted aryl group or an optionally substituted heteroaryl group, $R^{6a}$, $R^{7a}$, $R^{6b}$ and $R^{7b}$ are each absent, or a hydrogen atom, a lower alkyl group, a halogen atom or a cyano group, $R^{3a}$ and $R^{3b}$ are each an aminomethyl group optionally substituted by 1 or 2 lower alkyl groups, and $R^{8b}$ is absent or a hydrogen atom, a lower alkyl group, a halogen atom, a cyano group or an oxo group, excluding a compound represented by the formula

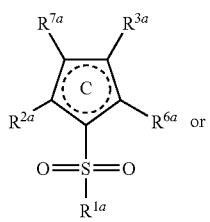

wherein each symbol is as defined above, or a salt thereof.

In compound (Ia), specific examples of ring C include 5-membered ring groups such as a thiophene ring, a furan ring, a pyrrole ring, an imidazole ring, a pyrazole ring, an isothiazole ring, a thiazole ring, an isoxazole ring, an oxazole ring, a pyrrolidine ring, a pyrroline ring, an imidazolidine ring, an imidazoline ring, a pyrazolidine ring, a pyrazoline ring, a furazan ring, an oxadiazole ring (e.g., 1,2,3-oxadiazole ring, 1,2,4-oxadiazole ring, 1,3,4-oxadiazole ring), a thiadiazole ring (e.g., 1,2,3-thiadiazole ring, 1,2,4-thiadiazole ring, 1,3,4-thiadiazole ring), a triazole ring (e.g., 1,2,3-triazole ring, 1,2,4-triazole ring), a tetrazole ring, a tetrahydrofuran ring, a cyclopentane ring, a cyclopentene ring, a cyclopentadiene ring and the like. Preferred are a pyrrole ring, an imidazole ring and a thiazole ring.

Here, the ring-constituting atom of ring C to which a group represented by $-SO_2-R^{1a}$ is bonded, the ring-constituting atom of ring C to which a substituent for $R^{2a}$ is bonded and the ring-constituting atom of ring C to which a substituent for $R^{3a}$ is bonded are each a carbon atom or a nitrogen atom.

The ring-constituting atom of ring C to which a substituent for $R^{6a}$ or $R^{7a}$ is bonded is a carbon atom, a nitrogen atom, an oxygen atom or a sulfur atom. When the ring-constituting atom of ring C to which a substituent for $R^{6a}$ or $R^{1a}$ is bonded is an oxygen atom or a sulfur atom, a substituent for $R^{6a}$ or $R^{7a}$ cannot be present, which means that these substituents are void. On the other hand, when the ring-constituting atom of ring C to which a substituent for $R^{6a}$ or $R^{7a}$ is bonded is a carbon atom or a nitrogen atom, $R^{6a}$ and $R^{7a}$ are each absent, or a hydrogen atom, a lower alkyl group, a halogen atom or a cyano group.

When the ring-constituting atom of ring C to which a substituent for $R^{6a}$ or $R^{7a}$ is bonded is a carbon atom or a nitrogen atom, a compound wherein $R^{6a}$ or $R^{7a}$ is absent is a compound wherein the ring-constituting atom of ring C to which a substituent for $R^{6a}$ or $R^{7a}$ is bonded is a nitrogen atom and a double bond is present between the nitrogen atom and a ring-constituting atom adjacent to the nitrogen atom.

Examples of the "lower alkyl group" for $R^{6a}$ or $R^{7a}$ include $C_{1-4}$ alkyl groups such as methyl, ethyl, propyl, isopropyl, butyl, isobutyl, sec-butyl, tert-butyl etc. and the like.

Examples of the "halogen atom" for $R^{6a}$ or $R^{7a}$ include a fluorine atom, a chlorine atom, a bromine atom and an iodine atom.

Examples of the $R^{1a}$, $R^{2a}$ and $R^{3a}$ include those similar to the above-mentioned groups exemplified for $R^1$, $R^2$ and $R^3$, respectively.

In compound (Ib), specific examples of ring D include 6-membered ring groups such as a pyridine ring, a pyrazine ring, a pyrimidine ring, a pyridazine ring, a piperidine ring, a piperazine ring, a morpholine ring, a thiomorpholine ring, a pyran ring, a thiopyran ring, a triazine ring (e.g., 1,2,4-triazine ring, 1,3,5-triazine ring), an oxazine ring (e.g., 1,4-oxazine ring, 1,3-oxazine ring), a thiazine ring (e.g., 1,4-thiazine ring, 1,3-thiazine ring), an oxadiazine ring, a thiadiazine ring, a tetrahydropyran ring, a tetrahydropyridine ring (e.g., 1,2,3,6-tetrahydropyridine ring), a dihydropyridine ring (e.g., 1,4-dihydropyridine ring), a cyclohexane ring, a cyclohexene ring, a cyclohexadiene ring, a benzene ring and the like. Preferred are a benzene ring, a pyridine ring and a pyrimidine ring.

Here, the ring-constituting atom of ring D to which a group represented by $-SO_2-R^{1b}$ is bonded, the ring-constituting atom of ring D to which a substituent for $R^{2b}$ is bonded and the ring-constituting atom of ring D to which a substituent for $R^{3b}$ is bonded are each a carbon atom or a nitrogen atom.

The ring-constituting atom of ring D to which a substituent for $R^{6b}$, $R^{7b}$ or $R^{8b}$ is bonded is a carbon atom, a nitrogen atom, an oxygen atom or a sulfur atom. When the ring-constituting atom of ring D to which a substituent for $R^{6b}$, $R^{7b}$ or $R^{8b}$ is bonded is an oxygen atom or a sulfur atom, a substituent for $R^{6b}$, $R^{7b}$ or $R^{8b}$ cannot be present, which means that these substituents are void. On the other hand, when the ring-constituting atom of ring D to which a substituent for $R^{6b}$, $R^{7b}$ or $R^{8b}$ is bonded is a carbon atom or a nitrogen atom, $R^{6b}$, $R^{7b}$ or $R^{8b}$ are each absent, or a hydrogen atom, a lower alkyl group, a halogen atom or a cyano group.

A compound wherein $R^{6b}$, $R^{7b}$ or $R^{8b}$ is absent is a compound wherein the ring-constituting atom of ring D to which a substituent for $R^{6b}$, $R^{7b}$ or $R^{8b}$ is bonded is a nitrogen atom and a double bond is present between the nitrogen atom and a ring-constituting atom adjacent to the nitrogen atom.

Examples of the "lower alkyl group" and "halogen atom" for $R^{6b}$, $R^{7b}$ or $R^{8b}$ include those similar to the above-mentioned "lower alkyl group" and "halogen atom" for $R^{6a}$ or $R^{7a}$.

Examples of the $R^{1b}$, $R^{2b}$ and $R^{3b}$ include those similar to the above-mentioned groups exemplified for $R^1$, $R^2$ and $R^3$, respectively.

Preferable specific examples of compound (Ia) having a 5-membered ring structure are shown below.

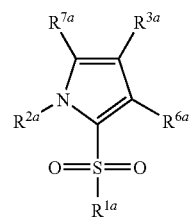 (Ia-1)

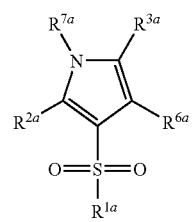 (Ia-2)

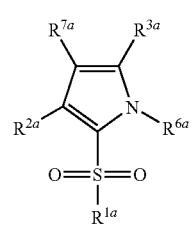 (Ia-3)

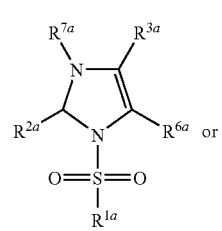 (Ia-4)

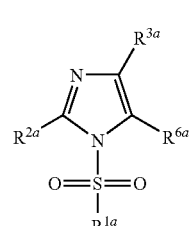 (Ia-5)

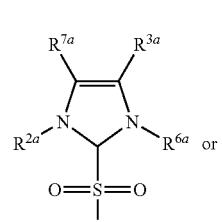 (Ia-6)

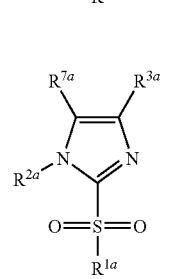 (Ia-7)

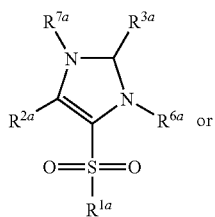 (Ia-8)
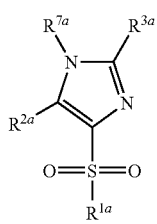 (Ia-9)
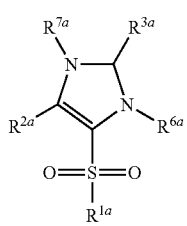 (Ia-10)
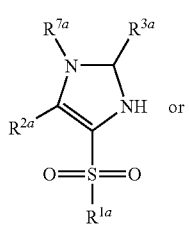 (Ia-11)
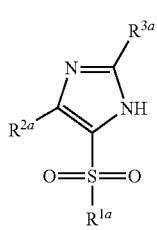 (Ia-12)
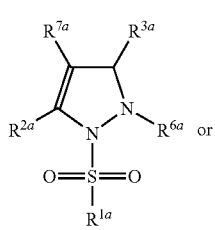 (Ia-13)
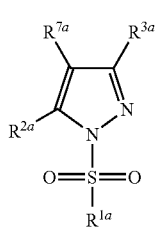 (Ia-14)
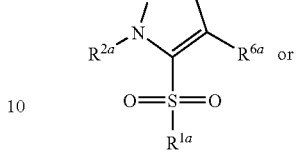 (Ia-15)
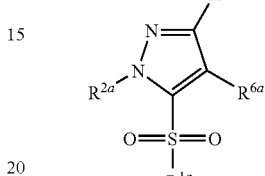 (Ia-16)
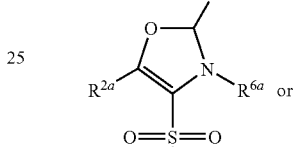 (Ia-17)
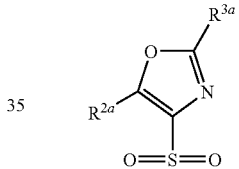 (Ia-18)
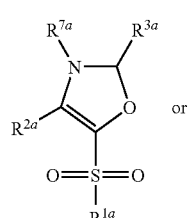 (Ia-19)
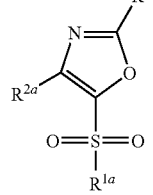 (Ia-20)
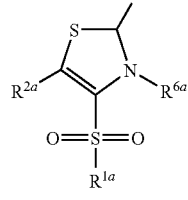 (Ia-21)

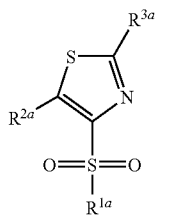 (Ia-22)
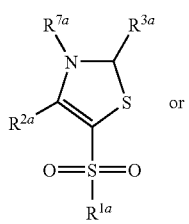 (Ia-23) or
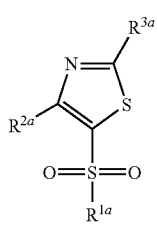 (Ia-24)
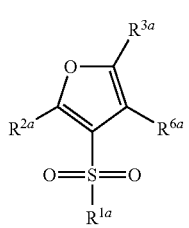 (Ia-25)
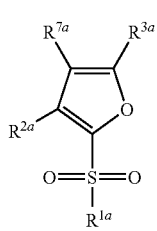 (Ia-26)
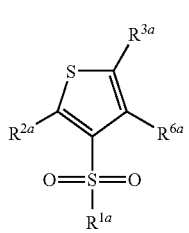 (Ia-27)
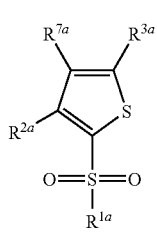 (Ia-28)
 (Ia-29)
 (Ia-30)
 (Ia-31) or
 (Ia-32)
 (Ia-33)
 (Ia-34)
 (Ia-35) or

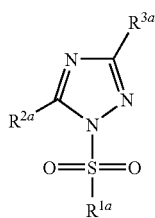
(Ia-36)
Each symbol in the formulas of the above-mentioned compounds (Ia-1)-(Ia-36) is as defined above.
Of the above, preferred are pyrrole ring, imidazole ring and thiazole ring derivatives represented by compounds (Ia-1)-(Ia-12) and (Ia-21)-(Ia-24).
Preferable specific examples of compound (Ib) having a 6-membered ring structure are shown below.
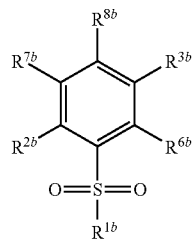
(Ib-1)
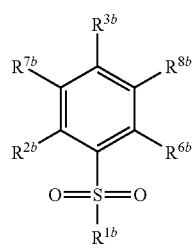
(Ib-2)
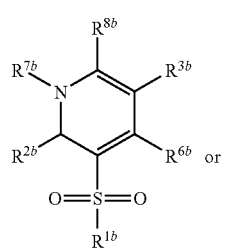
(Ib-3)
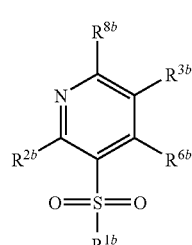
(Ib-4)
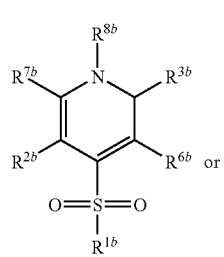
(Ib-5)
(Ib-6)
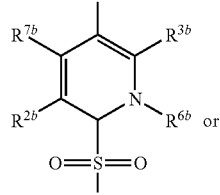
(Ib-7)
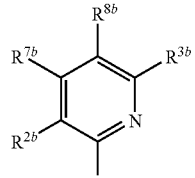
(Ib-8)
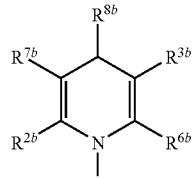
(Ib-9)
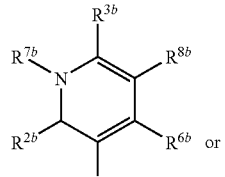
(Ib-10)
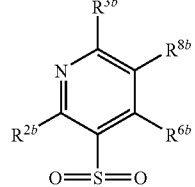
(Ib-11)
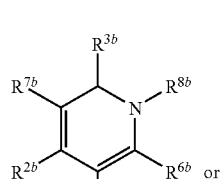
(Ib-12)

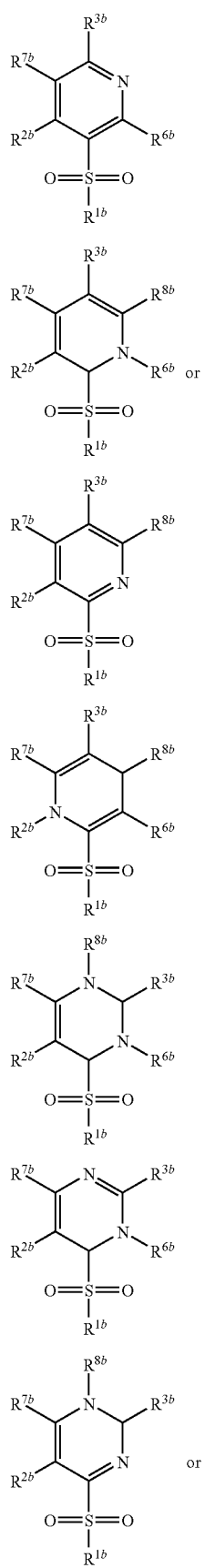
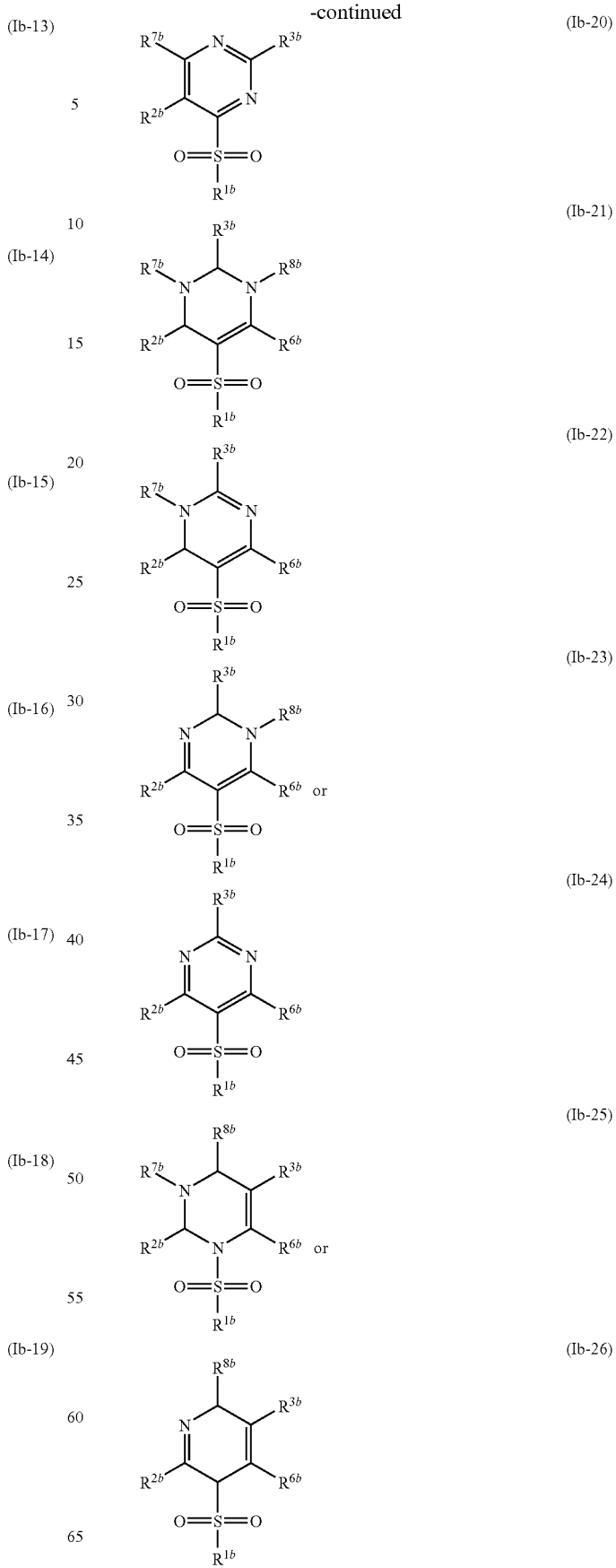

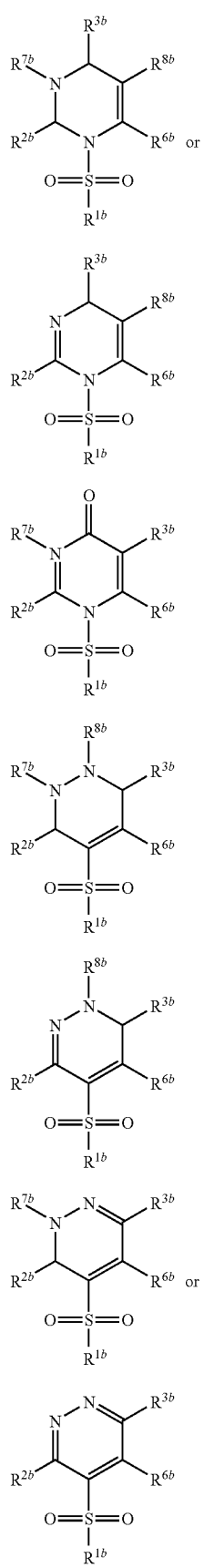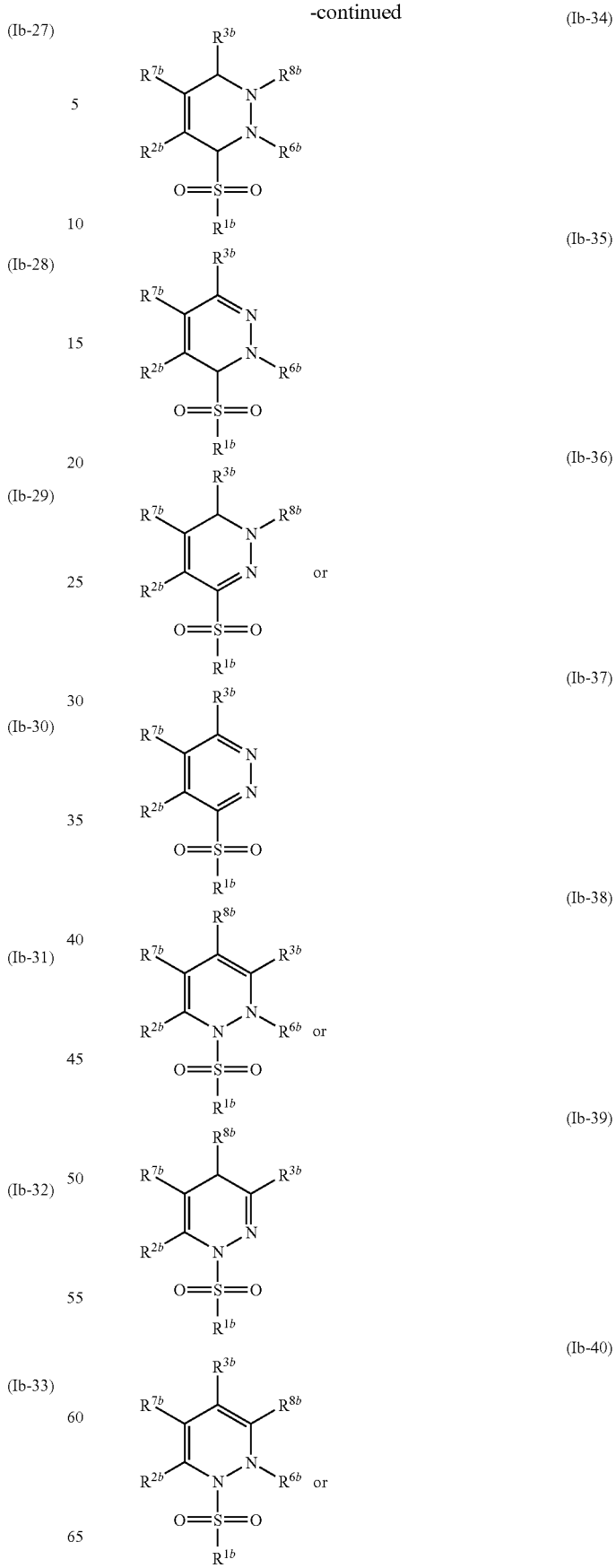

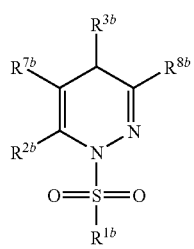

(Ib-41)

Each symbol in the formulas of the above-mentioned compounds (Ib-1)-(Ib-41) is as defined above.

Of the above, preferred are benzene ring, pyridine ring and pyrimidine ring derivatives represented by compounds (Ib-1)-(Ib-28).

In the above-mentioned compounds (I), (I'), (Ia), (Ib), (Ia-1)-(Ia-36) and (Ib-1)-(Ib-41), preferred as $R^1$, $R^{1a}$, $R^{1b}$ is a $C_{6-14}$ aryl group or a 5- or 6-membered aromatic heterocyclic group or a fused ring group thereof (e.g., a fused ring group of 5- or 6-membered aromatic heterocyclic group and a benzene ring or a 5- or 6-membered aromatic heterocycle) (e.g., $C_{6-14}$ aryl group such as phenyl, 1- or 2-naphthyl and the like; 5- or 6-membered aromatic heterocyclic group such as 2- or 3-thienyl, 2- or 3-furyl, 2- or 3-pyrrolyl, 2-, 4- or 5-oxazolyl, 2-, 4- or 5-thiazolyl, 2-, 4- or 5-imidazolyl, 3-, 4- or 5-isoxazolyl, 3-, 4- or 5-isothiazolyl, 3-, 4- or 5-pyrazolyl, 2-, 3- or 4-pyridyl, 2-, 4- or 5-pyrimidinyl, 3- or 4-pyridazinyl, 2-pyrazinyl and the like; fused ring group such as 2- or 3-benzofuryl, 2- or 3-benzothienyl, 1- or 3-isoindolyl, 2-benzimidazolyl, 2-benzooxazolyl, 3-benzoisoxazolyl, 2-benzothiazolyl, 3-benzoisothiazolyl, 2-, 3- or 4-quinolyl, 1-, 3- or 4-isoquinolyl, 3- or 4-cinnolinyl, 2- or 4-quinazolinyl, 2- or 3-quinoxalinyl, 1- or 4-phthalazinyl, naphthyridinyl, pteridinyl etc. and the like), which are optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) an amino group optionally substituted by $C_{1-6}$ alkyl (e.g., methyl, ethyl, propyl, isopropyl, butyl, isobutyl, sec-butyl, tert-butyl, pentyl, hexyl etc.), (vii) oxo, (viii) carbamoyl, (ix) mono-$C_{1-6}$ alkyl-carbamoyl (e.g., methylcarbamoyl, ethylcarbamoyl etc.), (x) di-$C_{1-6}$ alkyl-carbamoyl (e.g., dimethylcarbamoyl, diethylcarbamoyl, ethylmethylcarbamoyl etc.), (xi) $C_{1-6}$ alkylsulfonyl (e.g., methylsulfonyl, ethylsulfonyl etc.) and (xii) $C_{1-6}$ alkyl-carbonylamino (e.g., acetylamino etc.).

Among these, preferred is a phenyl group; a pyridyl group (e.g., 2-, 3- or 4-pyridyl) or a benzothienyl group (e.g., 2- or 3-benzothienyl), each optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) amino group optionally substituted by $C_{1-6}$ alkyl (e.g., methyl, ethyl, propyl, isopropyl, butyl, isobutyl, sec-butyl, tert-butyl, pentyl, hexyl etc.), (vii) oxo, (viii) carbamoyl, (ix) mono-$C_{1-6}$ alkyl-carbamoyl (e.g., methylcarbamoyl, ethylcarbamoyl etc.), (x) di-$C_{1-6}$ alkyl-carbamoyl (e.g., dimethylcarbamoyl, diethylcarbamoyl, ethylmethylcarbamoyl etc.), (xi) $C_{1-6}$ alkylsulfonyl (e.g., methylsulfonyl, ethylsulfonyl etc.) and (xii) $C_{1-6}$ alkyl-carbonylamino (e.g., acetylamino etc.), particularly preferably, a phenyl group or a pyridyl group each optionally substituted by 1 to 3 substituents selected from (i) halogen (e.g., fluorine, chlorine, bromine, iodine), (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine) and (iii) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine).

In the above-mentioned compounds (I), (I'), (Ia), (Ib), (Ia-1)-(Ia-36) and (Ib-1)-(Ib-41), preferable examples of the $R^2$, $R^{2a}$, $R^{2b}$ include [1] a $C_{6-14}$ aryl group (e.g., phenyl group) optionally substituted by 1 to 5 (preferably 1 to 3) substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) amino group optionally substituted by $C_{1-6}$ alkyl (e.g., methyl, ethyl, propyl, isopropyl, butyl, isobutyl, sec-butyl, tert-butyl, pentyl, hexyl etc.), (vii) carbamoyl, (viii) mono-$C_{1-6}$ alkyl-carbamoyl (e.g., methylcarbamoyl, ethylcarbamoyl etc.), (ix) di-$C_{1-6}$ alkyl-carbamoyl (e.g., dimethylcarbamoyl, diethylcarbamoyl, ethylmethylcarbamoyl etc.), (x) $C_{1-6}$ alkylsulfonyl (e.g., methylsulfonyl, ethylsulfonyl etc.) and (xi) $C_{1-6}$ alkyl-carbonylamino (e.g., acetylamino etc.), [2] a 5- 6-membered aromatic heterocyclic group or a fused ring group thereof (e.g., a fused ring group of a 5- or 6-membered aromatic heterocyclic group and a benzene ring or 5- 6-membered aromatic heterocycle) (e.g., 5- or 6-membered aromatic heterocyclic group such as 2- or 3-thienyl, 2- or 3-furyl, 2- or 3-pyrrolyl, 2-, 4- or 5-oxazolyl, 2-, 4- or 5-thiazolyl, 2-, 4- or 5-imidazolyl, 3-, 4- or 5-isoxazolyl, 3-, 4- or 5-isothiazolyl, 3-, 4- or 5-pyrazolyl, 2-, 3- or 4-pyridyl, 2-, 4- or 5-pyrimidinyl, 3- or 4-pyridazinyl, 2-pyrazinyl and the like; fused ring group such as 2- or 3-benzofuryl, 2- or 3-benzothienyl, 1- or 3-isoindolyl, 2-benzimidazolyl, 2-benzooxazolyl, 3-benzoisooxazolyl, 2-benzothiazolyl, 3-benzoisothiazolyl, 2-, 3- or 4-quinolyl, 1-, 3- or 4-isoquinolyl, 3- or 4-cinnolinyl, 2- or 4-quinazolinyl, 2- or 3-quinoxalinyl, 1- or 4-phthalazinyl, naphthyridinyl, pteridinyl etc. and the like) optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) amino group optionally substituted by $C_{1-6}$ alkyl (e.g., methyl, ethyl, propyl, isopropyl, butyl, isobutyl, sec-butyl, tert-butyl, pentyl, hexyl etc.), (vii) carbamoyl, (viii) mono-$C_{1-6}$ alkyl-carbamoyl (e.g., methylcarbamoyl, ethylcarbamoyl etc.), (ix)

di-$C_{1-6}$ alkyl-carbamoyl (e.g., dimethylcarbamoyl, diethylcarbamoyl, ethylmethylcarbamoyl etc.), (x) $C_{1-6}$ alkylsulfonyl (e.g., methylsulfonyl, ethylsulfonyl etc.) and (xi) $C_{1-6}$ alkyl-carbonylamino (e.g., acetylamino etc.), [3] $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine) and the like.

Among these, [1] a $C_{6-14}$ aryl group (e.g., phenyl group) optionally substituted by 1 to 5 (preferably 1 to 3) substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) amino group optionally substituted by $C_{1-6}$ alkyl (e.g., methyl, ethyl, propyl, isopropyl, butyl, isobutyl, sec-butyl, tert-butyl, pentyl, hexyl etc.), (vii) carbamoyl, (viii) mono-$C_{1-6}$ alkyl-carbamoyl (e.g., methylcarbamoyl, ethylcarbamoyl etc.), (ix) di-$C_{1-6}$ alkyl-carbamoyl (e.g., dimethylcarbamoyl, diethylcarbamoyl, ethylmethylcarbamoyl etc.), (x) $C_{1-6}$ alkylsulfonyl (e.g., methylsulfonyl, ethylsulfonyl etc.) and (xi) $C_{1-6}$ alkyl-carbonylamino (e.g., acetylamino etc.), [2] 2- or 3-thienyl or 2-, 3- or 4-pyridyl optionally substituted by 1 to 3 substituents selected from (i) halogen (e.g., fluorine, chlorine, bromine, iodine), (ii) hydroxy, (iii) cyano, (iv) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), (v) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1 to 5 (preferably 1 to 3) halogens (e.g., fluorine, chlorine, bromine, iodine), (vi) amino group optionally substituted by $C_{1-6}$ alkyl (e.g., methyl, ethyl, propyl, isopropyl, butyl, isobutyl, sec-butyl, tert-butyl, pentyl, hexyl etc.), (vii) carbamoyl, (viii) mono-$C_{1-6}$ alkyl-carbamoyl (e.g., methylcarbamoyl, ethylcarbamoyl etc.), (ix) di-$C_{1-6}$ alkyl-carbamoyl (e.g., dimethylcarbamoyl, diethylcarbamoyl, ethylmethylcarbamoyl etc.), (x) $C_{1-6}$ alkylsulfonyl (e.g., methylsulfonyl, ethylsulfonyl etc.) and (xi) $C_{1-6}$ alkyl-carbonylamino (e.g., acetylamino etc.), or [3] $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine) and the like is preferable. Furthermore, [1] a phenyl group optionally substituted by 1 to 5 (preferably 1 to 3) substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine), or [2] $C_{1-6}$ alkyl (e.g., methyl, ethyl, propyl, isopropyl, butyl, isobutyl, sec-butyl, tert-butyl, pentyl, hexyl etc.) optionally substituted by 1 to 5 (preferably 1 to 3) halogens (e.g., fluorine, chlorine, bromine, iodine) is preferable.

Particularly, preferred as $R^2$, $R^{2a}$, $R^{2b}$ is a phenyl group, a 2-fluorophenyl group or a 2-methylphenyl group; and $C_{1-6}$ alkyl (e.g., methyl, ethyl, propyl, isopropyl, butyl, isobutyl, sec-butyl, tert-butyl, pentyl, hexyl etc.).

In the above-mentioned compounds (I), (I'), (Ia), (Ib), (Ia-1)-(Ia-36) and (Ib-1)-(Ib-41), preferred as $R^3$, $R^{3a}$, $R^{3b}$ are an aminomethyl group (—$CH_2$—$NH_2$), a methylaminomethyl group (—$CH_2$—$NH(CH_3)$) and a dimethylaminomethyl group (—$CH_2$—$N(CH_3)_2$). Particularly, an aminomethyl group is preferable.

In the above-mentioned compounds (I), (I'), (Ia), (Ib), (Ia-1)-(Ia-36) and (Ib-1)-(Ib-41), preferred as $R^6$, $R^{6a}$, $R^{6b}$ are [1] absent (e.g., compounds (Ia-7), (Ia-9), (Ia-14), (Ia-18)-(Ia-20), (Ia-22)-(Ia-24), (Ia-26), (Ia-28), (Ia-31), (Ia-32), (Ia-35), (Ia-36), (Ib-8), (Ib-15), (Ib-19), (Ib-20), (Ib-36), (Ib-37), (Ib-39), (Ib-41) etc.), [2] a hydrogen atom, [3] a $C_{1-4}$ alkyl group such as methyl, ethyl, propyl, isopropyl, butyl, isobutyl, sec-butyl, tert-butyl and the like, [4] a halogen atom (e.g., fluorine, chlorine, bromine, iodine) and [5] a cyano group.

In the above-mentioned compounds (I'), (Ia), (Ib), (Ia-1)-(Ia-36) and (Ib-1)-(Ib-41), preferred as $R^7$, $R^{7a}$, $R^{7b}$ are [1] absent (e.g., compounds (Ia-5), (Ia-12), (Ia-16)-(Ia-18), (Ia-20)-(Ia-22), (Ia-24), (Ia-25), (Ia-27), (Ia-32), (Ia-36), (Ib-4), (Ib-11), (Ib-23), (Ib-24), (Ib-26), (Ib-28), (Ib-31), (Ib-33) etc.), [2] a hydrogen atom, [3] a $C_{1-4}$ alkyl group such as methyl, ethyl, propyl, isopropyl, butyl, isobutyl, sec-butyl, tert-butyl and the like, [4] a halogen atom (e.g., fluorine, chlorine, bromine, iodine) and [5] a cyano group.

In the above-mentioned compounds (I'), (Ib) and (Ib-1)-(Ib-41), preferred as $R^8$, $R^{8b}$ are [1] absent (e.g., compounds (Ib-6), (Ib-13), (Ib-18), (Ib-20), (Ib-22), (Ib-24), (Ib-32), (Ib-33), (Ib-35), (Ib-37) etc.), [2] an oxo group (e.g., compound (Ib-29)) or [3] a hydrogen atom and [4] a $C_{1-4}$ alkyl group such as methyl, ethyl, propyl, isopropyl, butyl, isobutyl, sec-butyl, tert-butyl etc. and the like.

In the above-mentioned compounds (I), (I'), (Ia), (Ib), (Ia-1)-(Ia-36) and (Ib-1)-(Ib-41), preferable embodiments of each substituent mentioned above can be freely combined.

As compound (I), N-methyl-1-[4-methyl-1-phenyl-5-(phenylsulfonyl)-1H-pyrrol-3-yl]methanamine, N,N-dimethyl-1-{1-[(4-methylphenyl)sulfonyl]-2-phenyl-1H-imidazol-4-yl}methanamine, 1-{1-[(3-methoxyphenyl)sulfonyl]-2-phenyl-1H-imidazol-4-yl}-N-methylmethanamine, N-methyl-1-[4-phenyl-5-(phenylsulfonyl)-1,3-thiazol-2-yl]methanamine or a salt thereof is particularly preferable.

Examples of the salt of compound (I) include metal salt, ammonium salt, salts with organic bases, salts with inorganic acids, salts with organic acids, salts with basic or acidic amino acids and the like. Preferable examples of metal salt include alkali metal salts such as sodium salt, potassium salt and the like; alkaline earth metal salts such as calcium salt, magnesium salt, barium salt and the like; aluminum salt and the like. Preferable examples of the salt with organic base include a salt with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include a salt with hydrochloric acid, hydrobromic acid, nitric acid, sulfuric acid, phosphoric acid and the like. Preferable examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include a salt with arginine, lysin, ornithine and the like. Preferable examples of the salt with acidic amino acid include a salt with aspartic acid, glutamic acid and the like.

Of these, pharmaceutically acceptable salts are preferable. For example, when a compound contains an acidic functional group, inorganic salts such as alkali metal salt (e.g., sodium salt, potassium salt etc.), alkaline earth metal salt (e.g., calcium salt, magnesium salt, barium salt etc.) and the like, ammonium salt and the like; and when a compound contains a basic functional group, for example, salts with inorganic acid such as hydrochloric acid, hydrobromic acid, nitric acid, sulfuric acid, phosphoric acid and the like, or salts with organic acid such as acetic acid, phthalic acid, fumaric acid, oxalic acid, tartaric acid, maleic acid, citric acid, succinic acid, methanesulfonic acid, p-toluenesulfonic acid and the like can be mentioned.

The production methods of compound (I) in the present invention are explained.

The compounds (II)-(XXI) in the formulas may form salts, and as such salts, for example, those similar to the salts of compound (I) can be mentioned.

In the formulas, n is an integer of 0, 1 and 2. When n is 0 or 1, each compound can be converted to a compound wherein n is 2 by oxidation with a suitable oxidant.

While the compounds obtained in the respective steps can be used for the next reaction in the form of a reaction mixture or a crude product, they can also be easily isolated and purified from the reaction mixture by a known separation and purification means, such as recrystallization, distillation, chromatography and the like.

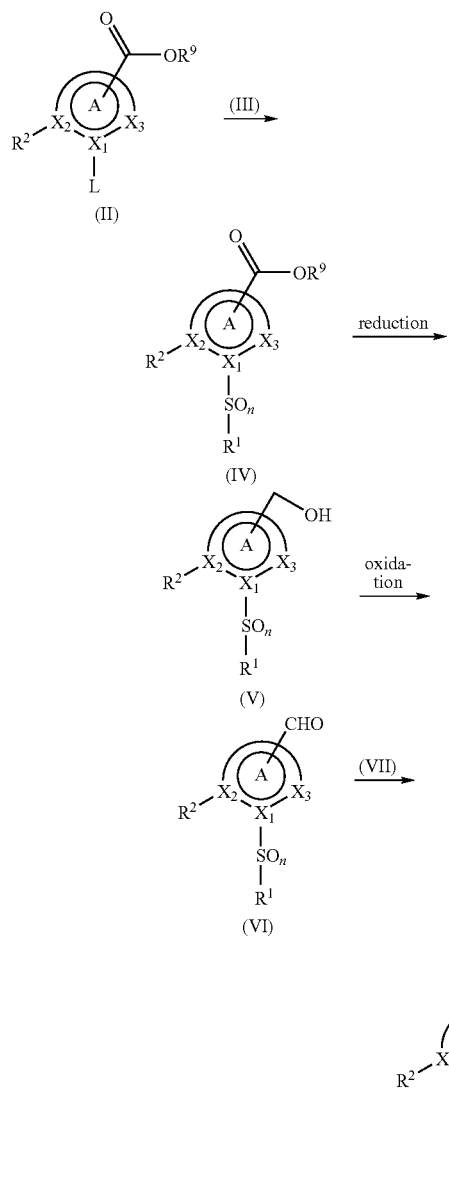

Compound (II) wherein $R^2$ is as defined above, $R^9$ is a $C_{1-4}$ alkyl group such as methyl, ethyl, propyl, isopropyl or butyl and the like, L is a hydrogen atom or a leaving group such as halogen (e.g., fluorine, chlorine, bromine, iodine), methanesulfonyloxy, p-toluenesulfonyloxy and the like may be a commercially available product, or can be produced according to a method known per se, for example, the methods described in J.C.S. Chem. Commun., page 26 (1983), J. Heterocyclic. Chem., vol. 13, page 1145 (1976), WO04/7478 and J. Med. Chem., vol. 35, page 4195 (1992), J. Org. Chem., vol. 39, page 1290 (1974) and the like, or a method analogous thereto.

Compound (IV) wherein each symbol is as defined above can be produced by reacting compound (II) with a compound represented by the formula (III)

wherein each symbol is as defined above, $X^1$ is a hydrogen atom or a leaving group such as halogen (e.g., fluorine, chlorine, bromine, iodine) and the like.

This reaction is advantageously performed using a solvent inert to the reaction. While the solvent is not particularly limited as long as the reaction proceeds, hydrocarbons such as benzene, toluene and the like, ethers such as tetrahydrofuran and the like, amides such as N,N-dimethylformamide, N,N-dimethylacetamide and the like, and the like or a mixed solvent thereof and the like are preferable.

Use of a base is effective for the reaction. As the base, for example, inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned. The amount of the base to be used is about 1 to about 10 mol, preferably about 1 to about 5 mol, per 1 mol of compound (II).

In addition, this reaction can be also performed in the co-presence of crown ether or a halogenating agent. Examples of the crown ether include 15-crown-5-ether, 18-crown-6-ether and the like, and examples of the halogenating agent include N-iodosuccinimide, N-bromosuccinimide, N-chlorosuccinimide, bromine and the like. The amount of these crown ether and halogenating agent to be used is each about 1-about 10 mol, preferably about 1-about 5 mol, per 1 mol of compound (II).

While the reaction time varies depending on the reagents and solvents to be used, it is generally about 30 min to about 24 hr, preferably about 30 min to about 8 hr. The reaction temperature is generally about 0° C. to about 100° C., preferably about 10° C. to about 50° C. In addition, this reaction can also be performed by a method similar to Org. Lett., vol. 6, page 4587 (2004) and Synlett, page 1254 (2004) and a method analogous thereto.

Compound (V) wherein each symbol in the formula is as defined above can be produced by reducing compound (IV) with a reducing agent such as lithium aluminum hydride, diisobutyl aluminum hydride, sodium borohydride, calcium borohydride and the like. As the reducing agent, diisobutyl aluminum hydride is particularly preferable. The amount of the reducing agent to be used is about 0.75 to about 10 equivalents, preferably about 1 to about 5 equivalents, per 1 mol of compound (IV).

This reaction is advantageously performed using a solvent inert to the reaction. While the solvent is not particularly limited as long as the reaction proceeds, solvents such as hydrocarbons (e.g., benzene, toluene and the like), ethers (e.g., tetrahydrofuran, diethyl ether and the like) and the like, a mixed solvent thereof and the like are preferable.

While the reaction time varies depending on the reagents and solvent to be used, it is generally about 30 min to about 24 hr, preferably about 30 min to about 8 hr.

The reaction temperature is generally about −78° C. to about 100° C., preferably about −78° C. to about 25° C.

Compound (VI) wherein each symbol in the formula is as defined above can be synthesized by reacting compound (V) with an oxidant such as chromic acid-pyridine complex, pyridinium chlorochromate, manganese dioxide, sulfur trioxide-pyridine complex, tetra-n-propylammonium perruthenate and the like. As the oxidant, manganese dioxide, sulfur trioxide-pyridine complex or tetra-n-propylammonium perruthenate is preferable. The oxidation reaction can be performed, for example, according to the method described in Synthesis, p. 639 (1994).

Compound (I) wherein each symbol is as defined above can be produced by subjecting compound (VI) and a compound represented by the formula (VII)

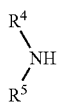

(VII)

wherein $R^4$ and $R^5$ are as defined above, to a reductive amination reaction according to, for example, the method described in Jikken Kagaku Koza (Courses in Experimental Chemistry), vol. 14-III, page 1380-1385 (1978), (Maruzen Press).

In each of the above-mentioned reaction steps for deriving compound (I) from compound (II), when desired, protection or deprotection, acylation reaction, alkylation reaction, hydrogenation reaction, oxidation reaction, reduction reaction, carbon chain extension reaction, substituent exchange reaction and the like may be applied individually or in a combination of two or more thereof to various intermediates, or, after deriving a compound encompassed in compound (I), the aforementioned reactions may be combined to further lead the compound to a desired embodiment.

The synthesis method of compound (Ia) is now explained.

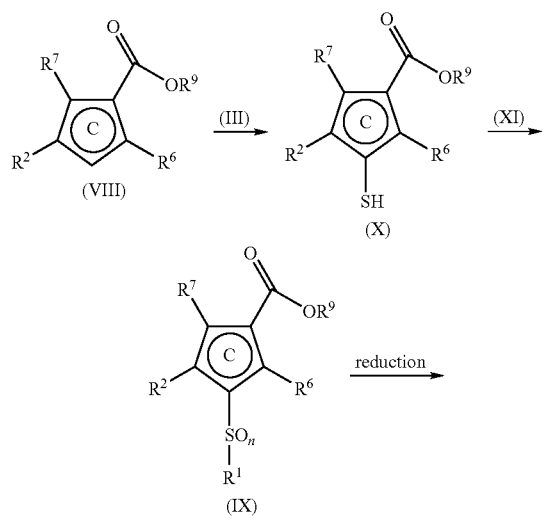

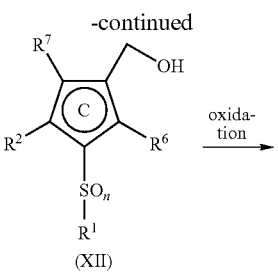

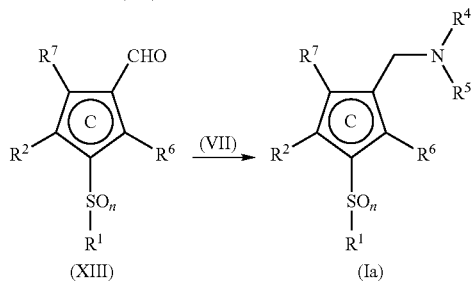

compounds (VIII) and (X) wherein $R^2$, $R^6$ and $R^7$ are as defined above, and $R^9$ is a $C_{1-4}$ alkyl group such as methyl, ethyl, propyl, isopropyl or butyl and the like may be commercially available products, or can be produced by a method known per se, for example, the methods described in J.C.S. Chem. Commun., page 26 (1983), J. Heterocyclic. Chem., vol. 13, page 1145 (1976), WO04/7478 and J. Med. Chem., vol. 35, page 4195 (1992) and the like, or a method analogous thereto.

Compound (IX) wherein each symbol is as defined above can be produced by reacting compound (VIII) with a compound represented by the formula (III)

(III)

wherein each symbol is as defined above, and $X^1$ is a hydrogen atom or a leaving group such as halogen (e.g., fluorine, chlorine, bromine, iodine) and the like.

This reaction is advantageously performed using a solvent inert to the reaction. While the solvent is not particularly limited as long as the reaction proceeds, hydrocarbons such as benzene, toluene and the like, ethers such as tetrahydrofuran and the like, amides such as N,N-dimethylformamide, N,N-dimethylacetamide and the like, and the like or a mixed solvent thereof and the like are preferable.

Use of a base is effective for the reaction. As the base, for example, inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned. The amount of the base to be used is about 1 to about 10 mol, preferably about 1 to about 5 mol, per 1 mol of compound (VIII).

In addition, this reaction can also be performed in the co-presence of crown ether or a halogenating agent. Examples of the crown ether include 15-crown-5-ether, 18-crown-6-ether and the like, and examples of the halogenating agent include N-iodosuccinimide, N-bromosuccinimide, N-chlorosuccinimide, bromine and the like. The amount of these crown ether and halogenating agent to be used is, about 1-about 10 mol, preferably about 1-about 5 mol, per 1 mol of compound (VIII), respectively.

While the reaction time varies depending on the reagents and solvent to be used, it is generally about 30 min to about 24 hr, preferably about 30 min to about 8 hr.

The reaction temperature is generally about 0° C. to about 100° C., preferably about 10° C. to about 50° C.

Compound (IX) can be produced by reacting compound (X) with a compound represented by the formula (XI)

$$R^1—X^2 \quad (XI)$$

wherein each symbol is as defined above, and $X^2$ is a leaving group such as halogen (e.g., fluorine, chlorine, bromine, iodine), methanesulfonyloxy and the like.

This reaction is advantageously performed using a solvent inert to the reaction. While the solvent is not particularly limited as long as the reaction proceeds, hydrocarbons such as benzene, toluene and the like, ethers such as tetrahydrofuran and the like, amides such as N,N-dimethylformamide, N,N-dimethylacetamide, N-methylpiperidone and the like, and the like or a mixed solvent thereof and the like are preferable.

Use of a base is effective for the reaction. As the base, for example, inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned. The amount of the base to be used is about 1 to about 10 mol, preferably about 1 to about 5 mol, per 1 mol of compound (X).

While the reaction time varies depending on the reagents and solvent to be used, it is generally about 30 min to about 24 hr, preferably about 30 min to about 8 hr.

The reaction temperature is generally about 0° C. to about 200° C., preferably about 10° C. to about 100° C.

Compound (XII) wherein each symbol is as defined above can be produced by reducing compound (IX) with a reducing agent such as lithium aluminum hydride, diisobutylaluminum hydride, sodium borohydride, calcium bis(borohydride) and the like. As the reducing agent, particularly diisobutylaluminum hydride is preferable. The amount of these reducing agents to be used is is about 0.75-about 10 equivalents, preferably about 1-about 5 equivalents, per 1 mol of compound (IX).

This reaction is advantageously performed using a solvent inert to the reaction. While the solvent is not particularly limited as long as the reaction proceeds, hydrocarbons such as benzene, toluene and the like, ethers such as tetrahydrofuran, diethyl ether and the like, and the like or a mixed solvent thereof and the like are preferable.

While the reaction time varies depending on the reagents and solvent to be used, it is generally about 30 min to about 24 hr, preferably about 30 min to about 8 hr.

The reaction temperature is generally about −78° C. to about 100° C., preferably about −78° C. to about 25° C.

compound (XIII) (wherein each symbol is as defined above) can be synthesized by reacting compound (XII) with an oxidant such as chromic acid.pyridine complex, pyridinium chlorochromate, manganese dioxide, sulfur trioxide.pyridine complex or tetra-n-propylammonium perruthenate and the like. As the oxidant, manganese dioxide, sulfur trioxide.pyridine complex or tetra-n-propylammonium perruthenate is preferable. This oxidation reaction can be performed, for example, according to the method described in Synthesis, p. 639 (1994).

Compound (Ia) (wherein each symbol is as defined above) can be produced by subjecting compound (XIII) and a compound represented by the formula (VII)

wherein $R^4$, $R^5$ are as defined above to a reductive amination reaction according to, for example, the method described in Jikken Kagaku Koza (Courses in Experimental Chemistry), vol. 14-III, pp. 1380-1385 (1978) (Maruzen Press).

In each of the above-mentioned reaction steps to derive compound (Ia) from compound (VIII) or (X), or each of the below-mentioned reaction steps to derive compound (Ia) from compound (XIV) or (XV), when desired, protection or deprotection, acylation reaction, alkylation reaction, hydrogenation reaction, oxidation reaction, reduction reaction, carbon chain extension reaction, substituent exchange reaction and the like may be applied individually or in a combination of two or more thereof to various intermediates, or, after deriving a compound encompassed in compound (Ia), the aforementioned reactions may be combined to further lead the compound to a desired embodiment.

Compounds (XIII) and (Ia) can also be produced by the following method.

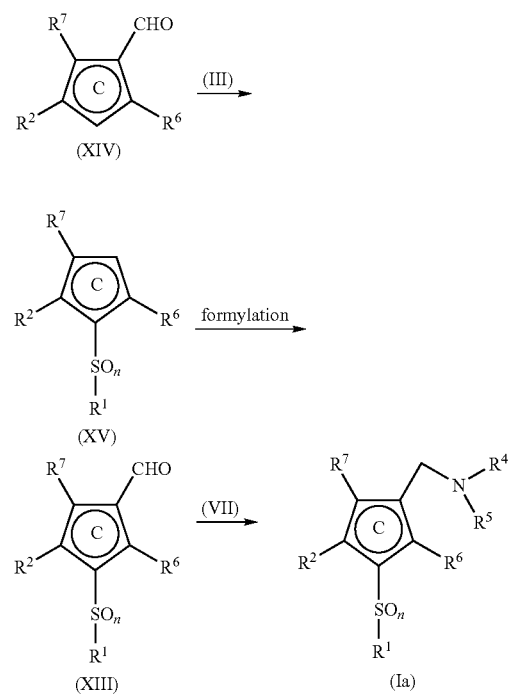

Compound (XIV) (wherein each symbol is as defined above) may be a commercially available product, or can be produced by a method known per se, for example, the methods described in J. Med. Chem., vol. 43, p. 2165 (2000), Tetrahedron, vol. 46, p. 7587 (1990) and Tetrahedron, vol. 57, p. 7813 (2001) and the like, or a method analogous thereto.

Compound (XIII) (wherein each symbol is as defined above) can be produced by treating compound (XIV) by a method for producing compound (IX) from compound (VIII) or a method analogous thereto, or treating compound (XV) by formylation according to a method described in, for example, 4th Ed. Jikken Kagaku Koza (Courses in Experimental Chemistry), vol. 21, pp. 106-124 (1991) (Maruzen Press) and the like or a method analogous thereto.

In addition, compound (Ia) can also be produced by the following method.

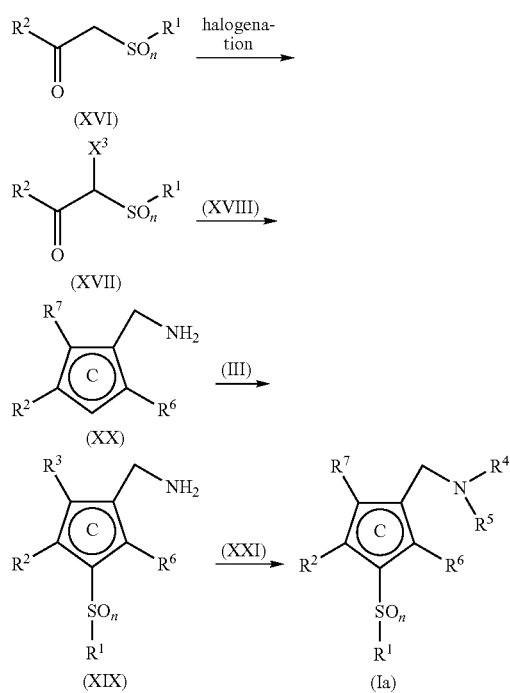

Compounds (XVI) and (XX) (wherein each symbol is as defined above) can be produced by a method known per se, for example, the methods described in J. Org. Chem., vol. 46, p. 2596 (1981) and Org. Lett., vol. 3, p. 1261 (2001) and the like, or a method analogous thereto.

Compound (XVII) (wherein each symbol is as defined above, and $X^3$ is a leaving group such as halogen (e.g., fluorine, chlorine, bromine, iodine) and the like) can be obtained by treating compound (XVI) with a halogen such as chlorine, bromine, iodine and the like or a metal halide such as copper (II) bromide, copper (II) chloride and the like.

The amount of halogen or metal halide to be used is about 1 to about 5 mol, preferably about 1 to about 2 mol, per 1 mol of compound (XVI).

This reaction is advantageously performed without solvent or in the presence of a solvent inert to the reaction. While the solvent is not particularly limited as long as the reaction proceeds, for example, ethers, esters, aromatic hydrocarbons, aliphatic hydrocarbon, amides, halogenated hydrocarbons, nitriles, sulfoxides, organic acids, aromatic amines or a mixture of two or more kinds thereof and the like are used.

This reaction can also be performed in the co-presence of an acid or base.

As the acid, for example, inorganic acids such as hydrochloric acid, hydrobromic acid and the like, and the like can be mentioned. As the base, for example, metal hydroxides such as sodium hydroxide, potassium hydroxide, lithium hydroxide and the like, basic salts such as sodium carbonate, potassium carbonate, cesium carbonate, sodium hydrogen carbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned. The amount of the acid to be used is about 0.01 to about 3 mol, preferably about 0.01 to about 1 mol, per 1 mol of compound (XVI). The amount of the base to be used is about 1 to about 10 mol, preferably about 1 to about 3 mol, per 1 mol of compound (XVI).

While the reaction time varies depending on the reagent and solvent to be used, it is generally about 5 min-about 24 hr, preferably about 10 min-about 5 hr.

The reaction temperature is generally about −20° C.-about 150° C., preferably about 0° C.-about 100° C.

Compound (XIX) can be obtained by condensing compound (XVII) and a compound represented by the formula (XVIII)

$$\underset{Y}{H_2N}\!\!\!-\!\!\!\!\diagdown\!\!\!-\!\!NH_2 \qquad (XVIII)$$

wherein Y is an oxygen atom, a sulfur atom or a nitrogen atom (NH).

When compound (XVIII) is commercially available, a commercially available product may be directly used, or obtained by a method known per se or a method analogous thereto and the like.

The amount of compound (XVIII) to be used is about 0.5 to about 3 mol, preferably about 0.8 to about 2 mol, per 1 mol of compound (XVII).

This reaction is advantageously performed without solvent or in the presence of a solvent inert to the reaction. While the solvent is not particularly limited as long as the reaction proceeds, for example, halogenated hydrocarbons, aliphatic hydrocarbons, aromatic hydrocarbons, ethers, amides, alcohols, nitrites or a mixture of two or more kinds thereof and the like are used.

When desired, this reaction can also be performed in the co-presence of a base. As the base, for example, basic salts such as sodium carbonate, potassium carbonate, cesium carbonate, sodium hydrogen carbonate, sodium acetate and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned. The amount of the base to be used is about 1 to about 30 mol, preferably about 1 to about 10 mol, per 1 mol of compound (XVII).

While the reaction time varies depending on the reagent and solvent to be used, it is generally about 5 min-about 72 hr, preferably about 0.5-about 30 hr.

The reaction temperature is generally about −5° C.-about 200° C., preferably about 5° C.-about 150° C.

Compound (XIX) (wherein each symbol is as defined above) can be produced by treating compound (XX) by a method for producing compound (IX) from compound (VIII) or a method analogous thereto.

Compound (Ia) (wherein each symbol is as defined above) can be produced by reacting compound (XIX) with a compound represented by the formula (XXI)

$$R^4—X^4 \quad (XXI)$$

wherein each symbol is as defined above, $X^4$ is a leaving group such as halogen (e.g., fluorine, chlorine, bromine, iodine), methanesulfonyloxy and the like.

This reaction is advantageously performed using a solvent inert to the reaction. While the solvent is not particularly limited as long as the reaction proceeds, hydrocarbons such as benzene, toluene and the like, ethers such as tetrahydrofuran and the like, amides such as N,N-dimethylformamide, N,N-dimethylacetamide and the like, and the like or a mixed solvent thereof and the like is preferable.

Use of a base is effective for the reaction. As the base, for example, inorganic bases such as sodium hydride, sodium hydroxide, potassium hydroxide and the like, basic salts such as sodium carbonate, potassium carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine and the like, and the like can be mentioned. The amount of the base to be used is about 1 to about 10 mol, preferably about 1 to about 5 mol, per 1 mol of compound (XIX).

While the reaction time varies depending on the reagents and solvent to be used, it is generally about 30 min to about 24 hr, preferably about 30 min to about 8 hr.

The reaction temperature is generally about −20° C. to about 100° C., preferably about 0° C. to about 50° C.

In each of the above-mentioned reaction step to derive compound (Ia) from compound (XVI) or (XX), when desired, protection or deprotection, acylation reaction, alkylation reaction, hydrogenation reaction, oxidation reaction, reduction reaction, carbon chain extension reaction, substituent exchange reaction and the like may be applied individually or in a combination of two or more thereof to various intermediates, or, after deriving a compound encompassed in compound (Ia), the aforementioned reactions may be combined to further lead the compound to a desired embodiment.

In each of the aforementioned reaction, when a starting material compound has an amino group, a carboxyl group or a hydroxyl group as a substituent, these groups may be protected by a protecting group generally used for peptide chemistry and the like. In this case, the object compound can be obtained by removing the protecting group as necessary after the reaction. Such protecting groups can be introduced or removed by a method known per se, for example, the method described in "Protective Groups in Organic Synthesis, 3rd Ed." (Theodora W. Greene, Peter G. M. Wuts, Wiley-Interscience (1999)) and the like.

Compound (I) can be isolated and purified by a known means such as phase transfer, concentration, solvent extraction, fractionation, liquid conversion, crystallization, recrystallization, chromatography and the like.

When compound (I) is obtained as a free compound, it can be converted to a desired salt by a method known per se or a method analogous thereto; conversely, when compound (I) is obtained as a salt, it can be converted into a free form or another desired salt by a method known per se or a method analogous thereto.

Compound (I) may be used as a prodrug. The prodrug of compound (I) means a compound which is converted to compound (I) under the physiological condition in the body by a reaction with an enzyme, gastric acid, or the like, that is, a compound which is converted to compound (I) by enzymatic oxidation, reduction, hydrolysis, and the like; a compound which is converted to compound (I) by hydrolysis and the like with gastric acid, and the like.

The prodrug of compound (I) includes a compound wherein the amino group of compound (I) is modified with acyl, alkyl or phosphoryl (e.g., a compound wherein the amino group of compound (I) is modified with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl or t-butyl, etc.); a compound wherein the hydroxyl group of compound (I) is modified with acyl, alkyl, phosphoryl or borate (e.g., a compound wherein the hydroxyl group of compound (I) is modified with acetyl, palmitoyl, propanoyl, pivaloyl, succinyl, fumaryl, alanyl or dimethylaminomethylcarbonyl, etc.); a compound wherein a carboxyl group of compound (I) is modified to ester or amide (e.g., a compound wherein a carboxyl group of compound (I) is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester or methylamide, etc.); and the like. These compounds can be produced from compound (I) by a method known per se.

In addition, the prodrug of compound (I) may be a compound, which is converted to compound (I) under the physiological conditions, as described in Pharmaceutical Research and Development, Vol. 7 (Molecule Design), pp. 163-198 (1990), published by Hirokawa Publishing Co.

When compound (I) contains isomers such as an optical isomer, a stereoisomer, a regioisomer, a rotamer and the like, any of these isomers and a mixture of these are also encompassed in compound (I). For example, when compound (I) has an optical isomer, an optical isomer resolved from a racemate is also encompassed in compound (I). These isomers can be obtained as single products according to synthesis and separation methods known per se (concentration, solvent extraction, column chromatography, recrystallization, etc.)

The compound (I) may be a crystal, and both a single crystalline form and crystalline form mixture are encompassed in compound (I). Crystals can be produced by crystallization according to crystallization methods known per se.

The compound (I) may be a solvate (e.g., hydrate etc.) or a non-solvate, both of which are encompassed in the compound (I). A compound labeled with an isotope (e.g., $^3H$, $^{14}C$, $^{35}S$, $^{125}I$ and the like) is also encompassed in the compound (I).

Compound (I) and a prodrug thereof of the present invention (hereinafter sometimes to be abbreviated as the compound of the present invention) have a proton pump inhibitory action and effectively suppress gastric acid secretion. In addition, since they show low toxicity (e.g., acute toxicity, chronic toxicity, genetic toxicity, reproductive toxicity, cardiotoxicity, drug interaction, carcinogenicity and the like) and high water-solubility, and are superior in the stability, in vivo kinetics (absorbability, distribution, metabolism, excretion and the like), and efficacy expression, they are useful as pharmaceutical agents.

The compound of the present invention is useful for the prophylaxis or treatment of peptic ulcer (e.g., gastric ulcer, gastric ulcer due to postoperative stress, duodenal ulcer, anastomotic ulcer, ulcer caused by non-steroidal anti-inflammatory agent etc.); gastritis; erosive esophagitis; nonerosive esophagitis; reflux esophagitis such as erosive reflux esophagitis and the like; symptomatic gastroesophageal reflux disease (Symptomatic GERD) such as nonerosive esophageal reflux, esophageal reflux unaccompanied by esophagitis and the like; functional dyspepsia including NUD (Non Ulcer Dyspepsia); gastric cancer (including gastric cancer associated with promoted production of interleukin-1β due to gene polymorphism of interleukin-1); stomach MALT lymphoma; Zollinger-Ellison syndrome; hyperacidity; upper gastrointestinal hemorrhage caused by peptic ulcer, acute stress ulcer, hemorrhagic gastritis, invasive stress (e.g., stress caused by major surgery requiring post-operative intensive management, or cerebrovascular disorder, head trauma, multiple organ failure or extensive burn requiring intensive treatment) and the like; airway disorders; asthma; and the like, pre-anesthetic administration, eradication or assistant to eradication of *Helicobacter pylori* and the like in mammals (e.g., human, monkey, sheep, bovine, horse, dog, cat, rabbit, rat, mouse etc.).

As used herein, the above-mentioned reflux esophagitis and symptomatic gastroesophageal reflux disease (symptomatic GERD) are sometimes collectively referred to simply as GERD.

The content of a compound of the present invention in the pharmaceutical composition of the present invention is about 0.01 to 100% by weight relative to the entire composition. Though subject to change depending on the administration target, administration route, target disease and the like, its dose is about 0.5 to 1,500 mg/day, preferably about 5 to 150 mg/day, based on the active ingredient, when, for example, the compound is orally administered as an anti-ulcer agent to an adult human (60 kg). The compound of the present invention may be administered once daily or in 2 or 3 divided portions per day.

The compound of the present invention shows low toxicity and can be safely administered orally or parenterally (e.g., topical, rectal, intravenous administrations and the like) as it is or as a preparation containing a pharmaceutical composition containing a pharmacologically acceptable carrier admixed according to a method known per se, such as tablets (including sugar-coated tablets and film-coated tablets), powder, granule, capsule (including soft capsule), orally disintegrating tablet, orally disintegrating film, liquid, injection, suppository, sustained-release preparation, plaster and the like. Particularly, the compound of the present invention is preferably administered as an oral preparation in the form of tablet, granule, capsule and the like.

The pharmacologically acceptable carrier that may be used to produce the pharmaceutical composition of the present invention includes various organic or inorganic carrier substances in common use as pharmaceutical materials, including excipients, lubricants, binders, disintegrants, water-soluble polymers and basic inorganic salts for solid preparations; and solvents, solubilizing agents, suspending agents, isotonizing agents, buffers and soothing agents for liquid preparations and the like. Other ordinary additives such as preservatives, anti-oxidants, colorants, sweetening agents, souring agents, bubbling agents and flavorings may also be used as necessary.

Such "excipients" include, for example, lactose, sucrose, D-mannitol, starch, cornstarch, crystalline cellulose, light anhydrous silicic acid, titanium oxide and the like.

Such "lubricants" include, for example, magnesium stearate, sucrose fatty acid esters, polyethylene glycol, talc, stearic acid and the like.

Such "binders" include, for example, hydroxypropyl cellulose, hydroxypropylmethyl cellulose, crystalline cellulose, starch, polyvinylpyrrolidone, gum arabic powder, gelatin, pullulan, low-substituted hydroxypropyl cellulose and the like.

Such "disintegrants" include (1) crosspovidone, (2) what is called super-disintegrants such as crosscarmellose sodium (FMC-Asahi Chemical) and carmellose calcium (Gotoku Yakuhin) etc, (3) sodium carboxymethyl starch (e.g., product of Matsutani Chemical), (4) low-substituted hydroxypropyl cellulose (e.g., product of Shin-Etsu Chemical), (5) corn starch, and so forth. Said "crosspovidone" may be any crosslinked polymer having the chemical name 1-ethenyl-2-pyrrolidinone homopolymer, including polyvinylpyrrolidone (PVPP) and 1-vinyl-2-pyrrolidinone homopolymer, and is exemplified by Colidon CL (produced by BASF), Polyplasdon XL (produced by ISP), Polyplasdon XL-10 (produced by ISP), Polyplasdon INF-10 (produced by ISP) and the like.

Such "water-soluble polymers" include, for example, ethanol-soluble water-soluble polymers [e.g., cellulose derivatives such as hydroxypropyl cellulose (hereinafter also referred to as HPC) etc, polyvinylpyrrolidone and the like], ethanol-insoluble water-soluble polymers [e.g., cellulose derivatives such as hydroxypropylmethyl cellulose (hereinafter also referred to as HPMC) etc., methyl cellulose, carboxymethyl cellulose sodium and the like, sodium polyacrylate, polyvinyl alcohol, sodium alginate, guar gum and the like] and the like.

Such "basic inorganic salts" include, for example, basic inorganic salts of sodium, potassium, magnesium and/or calcium. Preferred are basic inorganic salts of magnesium and/or calcium. More preferred are basic inorganic salts of magnesium. Such basic inorganic salts of sodium include, for example, sodium carbonate, sodium hydrogen carbonate, disodium hydrogenphosphate and the like. Such basic inorganic salts of potassium include, for example, potassium carbonate, potassium hydrogencarbonate and the like. Such basic inorganic salts of magnesium include, for example, heavy magnesium carbonate, magnesium carbonate, magnesium oxide, magnesium hydroxide, magnesium aluminometasilicate, magnesium silicate, magnesium aluminate, synthetic hydrotalcite [$Mg_6Al_2(OH)_{16} \cdot CO_3 \cdot 4H_2O$], and magnesia alumina hydrate. Preferred are heavy magnesium carbonate, magnesium carbonate, magnesium oxide, magnesium hydroxide and the like. Such basic inorganic salts of calcium include, for example, precipitated calcium carbonate, calcium hydroxide, etc.

Such "solvents" include, for example, water for injection, alcohol, propylene glycol, macrogol, sesame oil, corn oil, olive oil and the like.

Such "solubilizing agents" include, for example, polyethylene glycol, propylene glycol, D-mannitol, benzyl benzoate, ethanol, trisaminomethane, cholesterol, triethanolamine, sodium carbonate, sodium citrate and the like.

Such "suspending agents" include, for example, surfactants such as stearyltriethanolamine, sodium lauryl sulfate, laurylaminopropionic acid, lecithin, benzalkonium chloride, benzethonium chloride, glyceryl monostearate etc; hydrophilic polymers such as polyvinyl alcohol, polyvinylpyrrolidone, carboxymethyl cellulose sodium, methyl cellulose, hydroxymethyl cellulose, hydroxyethyl cellulose, hydroxypropyl cellulose etc., and the like.

Such "isotonizing agents" include, for example, glucose, D-sorbitol, sodium chloride, glycerol, D-mannitol and the like.

Such "buffers" include, for example, buffer solutions of phosphates, acetates, carbonates, citrates etc, and the like.

Such "soothing agents" include, for example, benzyl alcohol and the like.

Such "preservatives" include, for example, p-oxybenzoic acid esters, chlorobutanol, benzyl alcohol, phenethyl alcohol, dehydroacetic acid, sorbic acid and the like.

Such "antioxidants" include, for example, sulfites, ascorbic acid, α-tocopherol and the like.

Such "colorants" include, for example, food colors such as Food Color Yellow No. 5, Food Color Red No. 2, Food Color Blue No. 2 etc.; food lake colors, red ferric oxide and the like.

Such "sweetening agents" include, for example, saccharin sodium, dipotassium glycyrrhizinate, aspartame, stevia, thaumatin and the like.

Such "souring agents" include, for example, citric acid (citric anhydride), tartaric acid, malic acid and the like.

Such "bubbling agents" include, for example, sodium bicarbonate and the like.

Such "flavorings" may be synthetic substances or naturally occurring substances, and include, for example, lemon, lime, orange, menthol, strawberry and the like.

The compound of the present invention may be prepared as a preparation for oral administration in accordance with a commonly-known method, by, for example, compression-shaping with a carrier such as an excipient, a disintegrant, a binder, a lubricant, or the like, and subsequently coating the preparation as necessary by a commonly known method for the purpose of taste masking, enteric dissolution or sustained release. For an enteric preparation, an intermediate layer may be provided by a commonly known method between the enteric layer and the drug-containing layer for the purpose of separation of the two layers.

For preparing the compound of the present invention as an orally disintegrating tablet, available methods include, for example, a method in which a core containing crystalline cellulose and lactose is coated with the compound of the present invention and, where necessary, a basic inorganic salt, and then further coated with a coating layer containing a water-soluble polymer to give a composition, which is coated with an enteric coating layer containing polyethylene glycol, further coated with an enteric coating layer containing triethyl citrate, still further coated with an enteric coating layer containing polyethylene glycol, and finally coated with mannitol to give fine granules, which are mixed with additives and shaped.

The above-mentioned "enteric coating layer" includes, for example, a layer consisting of a mixture of one or more kinds from aqueous enteric polymer substrates such as cellulose acetate phthalate (CAP), hydroxypropylmethyl cellulose phthalate, hydroxymethyl cellulose acetate succinate, methacrylic acid copolymers (e.g., Eudragit L30D-55 (trade name; produced by Rohm), Colicoat MAE30DP (trade name; produced by BASF), Polyquid PA30 (trade name; produced by San-yo Chemical) etc.), carboxymethylethyl cellulose, shellac and the like; sustained-release substrates such as methacrylic acid copolymers (e.g., Eudragit NE30D (trade name), Eudragit RL30D (trade name), Eudragit RS30D (trade name), etc.) and the like; water-soluble polymers; plasticizers such as triethyl citrate, polyethylene glycol, acetylated monoglycerides, triacetin, castor oil and the like; and the like, and the like.

The above-mentioned "additive" includes, for example, water-soluble sugar alcohols (e.g., sorbitol, mannitol, maltitol, reduced starch saccharides, xylitol, reduced palatinose, erythritol, etc.), crystalline cellulose (e.g., Ceolas KG 801, Avicel PH 101, Avicel PH 102, Avicel PH 301, Avicel PH 302, Avicel RC-591 (crystalline cellulose.carmellose sodium) etc.), low-substituted hydroxypropyl cellulose (e.g., LH-22, LH-32, LH-23, LH-33 (Shin-Etsu Chemical), mixtures thereof etc.) and the like. Furthermore, binders, souring agents, bubbling agents, sweetening agents, flavorings, lubricants, colorants, stabilizers, excipients, disintegrants etc. are also used.

The compound of the present invention may be used in combination with 1 to 3 other active ingredients.

Such "other active ingredients" include, for example, anti-*Helicobacter pylori* active substances, imidazole compounds, bismuth salts, quinolone compounds, and so forth.

Examples of the "anti-*Helicobacter pylori* active substance" include penicillin antibiotic (e.g., amoxicillin, benzylpenicillin, piperacillin, mecillinam etc.), cephem antibiotic (e.g., cefixime, cefaclor etc.), macrolide antibiotic (e.g., erythromycin, clarithromycin etc.), tetracycline antibiotic (e.g., tetracycline, minocycline, streptomycin etc.), aminoglycoside antibiotic (e.g., gentamicin, amikacin etc.), imipenem and the like. Of these, penicillin antibiotic, macrolide antibiotic and the like are preferable.

Such "imidazole compounds" include, for example, metronidazole, miconazole and the like.

Such "bismuth salts" include, for example, bismuth acetate, bismuth citrate and the like.

Such "quinolone compounds" include, for example, ofloxacin, ciploxacin and the like.

Particularly, for eradication of *Helicobacter pylori*, a compound (I) or a salt thereof of the present invention with antibiotic penicillin (e.g., amoxicillin and the like) and antibiotic erythromycin (e.g., clarithromycin and the like) is preferably used.

For the purpose of eradication of *Helicobacter pylori*, the compound of the present invention can enhance antibacterial action of other antibiotics based on the pH controlling action in the stomach and the like, and also provides an assistant effect such as an eradication effect based on the action of the antibiotics to be used in combination.

Such "other active ingredients" and the compound (I) or a salt thereof of the present invention may be mixed, prepared as a single pharmaceutical composition [e.g., tablets, powders, granules, capsules (including soft capsules), liquids, injectable preparations, suppositories, sustained-release preparations, etc.], in accordance with a commonly known method, and used in combination, and may also be prepared as separate preparations and administered to the same subject simultaneously or at a time interval.

In addition, the compound of the present invention may be used in combination with a gastric motility enhancer, a drug acting on lower esophageal sphincter (e.g., temporary lower esophageal sphincter relaxation suppressant etc.), ClC-2 channel opener (intestinal juice secretion enhancer), a histamine $H_2$ receptor antagonist, an antacid, a sedative, a stomachic digestant or a non-steroidal anti-inflammatory drug (NSAID).

As the "gastric motility enhancer", for example, domperidone, metoclopramide, mosapride, itopride, tegaserod and the like can be mentioned.

As the "a drug acting on lower esophageal sphincter", for example, GABA-B receptor agonists such as baclofen, an optically active form thereof etc., and the like can be mentioned.

As the "ClC-2 channel opener (intestinal juice secretion enhancer)", lubiprostone and the like can be mentioned.

As the "histamine H₂ receptor antagonist", cimetidine, ranitidine, famotidine, roxatidine, nizatidine, lafutidine and the like can be mentioned.

As the "antacid", sodium hydrogen carbonate, aluminum hydroxide and the like can be mentioned.

As the "sedatives", diazepam, chlordiazepoxide and the like can be mentioned.

As the "stomachic digestant", *gentiana, swertia japonica*, diastase and the like can be mentioned.

As the "non-steroidal anti-inflammatory drug", for example, aspirin, indomethacin, ibuprofen, mefenamic acid, diclofenac, etodorac, piroxicam, celecoxib and the like can be mentioned.

A gastric motility enhancer, a drug acting on lower esophageal sphincter, a ClC-2 channel opener (intestinal juice secretion enhancer), a histamine H₂ receptor antagonist, an antacid, a sedative, a stomachic digestant or a non-steroidal anti-inflammatory drug and compound (I) or a salt thereof of the present invention may be mixed, prepared as a single pharmaceutical composition [e.g., tablets, powders, granules, capsules (including soft capsules), liquids, injections, suppositories, sustained-release preparations, etc.] according to a method known per se for combined use, or may also be prepared as separate preparations and administered to the same subject simultaneously or in a staggered manner.

The compound of the present invention may be used in combination with the following drugs.

(i) proton pump inhibitor, for example, omeprazole, esomeprazole, pantoprazole, rabeprazole, tenatoprazole, ilaprazole and lansoprazole;

(ii) oral antacid combination agent, for example, Maalox, Aludrox and Gaviscon;

(iii) mucous membrane protector, for example, polaprezinc, ecabe sodium, rebamipide, teprenone, cetraxate, sucralfate, chloropylline-copper and plaunotol;

(iv) antigastric agent, for example, anti-gastrin vaccine, itriglumide and Z-360;

(v) 5-HT₃ antagonist, for example, dolasetron, palonosetron, alosetron, azasetron, ramosetron, mitrazapine, granisetron, tropisetron, E-3620, ondansetron and indisetron;

(vi) 5-HT₄ agonist, for example, tegaserod, mosapride, cinitapride and oxtriptane;

(vii) laxative agent, for example, Trifyba, Fybogel, Konsyl, Isogel, Regulan, Celevac and Normacol;

(viii) GABA$_B$ agonist, for example, baclofen and AZD-3355;

(ix) GABA$_B$ antagonist, for example, GAS-360 and SGS-742;

(x) calcium channel blocker, for example, aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine and fasudil;

(xi) dopamine antagonist, for example, metoclopramide, domperidone and levosulpiride;

(xii) tachykinin (NK) antagonist, particularly, NK-3, NK-2 and NK-1 antagonist, for example, nepadutant, saredutant, talnetant, ((R,9R)-7-[3,5-bis(trifluoromethyl)benzyl]-8,9,10,11-tetrahydro-9-methyl-5-(4-methylphenyl)-7H-[1,4]diazocino[2,1-g][1,7]naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine (2S,3S);

(xiii) nitric monoxide synthase inhibitor, for example, GW-274150, tilarginine, P54, guanidioethyldisulfide and nitroflurbiprofen;

(xiv) vanilloid receptor 1 antagonist, for example, AMG-517 and GW-705498;

(xv) ghrelin agonist, for example, capromorelin and TZP-101;

(xvi) AchE release stimulant, for example, Z-338 and KW-5092.

The above-mentioned drugs (i)-(xvi) and compound (I) or a salt thereof of the present invention may be mixed, prepared as a single pharmaceutical composition [e.g., tablets, powders, granules, capsules (including soft capsules), liquids, injections, suppositories, sustained-release preparations, etc.] according to a method known per se for combined use, or may also be prepared as separate preparations and administered to the same subject simultaneously or in a staggered manner.

EXAMPLES

The present invention is explained in detail in the following by referring to Reference Examples, Examples and Experimental Examples, which are not to be construed as limitative.

In the following Reference Examples and Examples, the "room temperature" generally means about 10° C. to about 35° C., but it is not particularly strictly limited. The mixing ratio of liquids shows a volume ratio. Unless otherwise specified, "%" means weight %. The yield is in mol/mol %. Silica gel column chromatography was performed using silica gel 60 (0.063-0.200 mm) manufactured by MERCK, Fuji Silysia Chemical Ltd. Chromatorex (trade name) NH (described as basic silica gel column chromatography). For ¹H-NMR spectrum, tetramethylsilane was used as the internal standard, and Varian Gemini-200 (200 MHz), Mercury-300 (300 MHz) spectrometer, Bruker AVANCE AV300 (300 MHz) and JNM-AL400 (400 MHz) nuclear magnetic resonance apparatuses JEOL DATUM (JEOL DATUM LTD.) were used for the measurement. The following abbreviations are used for showing the measurement results.

s: singlet, d: doublet, dd: double doublet, dt: double triplet, t: triplet, q: quartet, m: multiplet, br: broad, brs: broad singlet, J: coupling constant, Hz: Hertz.

Reference Example 1

Methyl 4-methyl-1H-pyrrole-3-carboxylate

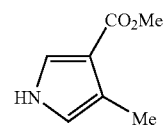

To a suspension of potassium tert-butoxide (76.7 g) in tetrahydrofuran (900 mL) was added dropwise a solution of p-toluenesulfonylmethyl isocyanide (94.6 g) and methyl crotonate (48.5 g) in tetrahydrofuran (900 mL) over 30 min. The reaction mixture was stirred at room temperature for 3 hr, water was added, and the mixture was extracted with ethyl acetate. The extract was washed with saturated brine, dried over anhydrous sodium sulfate, filtered and concentrated under reduced pressure. The residue was purified by silica gel column chromatography (eluent:hexane-ethyl acetate=4:1) to give the title compound as a white solid (yield 16.8 g, 25%).

¹H-NMR (CDCl₃) δ: 2.29 (3H, s), 3.80 (3H, s), 6.53-6.54 (1H, m), 7.36-7.38 (1H, m), 8.25 (1H, brs).

Reference Example 2

Methyl 4-methyl-1-phenyl-1H-pyrrole-3-carboxylate

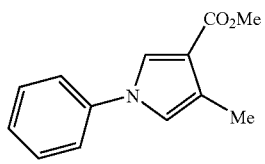

To a solution of methyl 4-methyl-1H-pyrrole-3-carboxylate (1.70 g) in N,N-dimethylformamide (1.5 mL) were added iodobenzene (1.50 mL), potassium carbonate (2.19 g), L-proline (273 mmg) and copper iodide (232 mg), and the reaction was carried out in a microwave reactor (Emrys Optimizer manufactured by Personal Chemistry, 70° C., 1 hr). The reaction mixture was filtered through celite, water was added to the filtrate, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=9:1→2:1) to give the title compound as a colorless solid (yield 925 mg, 35%).

¹H-NMR (CDCl₃) δ: 2.33 (3H, s), 3.82 (3H, s), 6.80-6.85 (1H, m), 7.20-7.50 (5H, m), 7.60-7.65 (1H, m).

Reference Example 3

Methyl 4-methyl-1-phenyl-5-(phenylthio)-1H-pyrrole-3-carboxylate

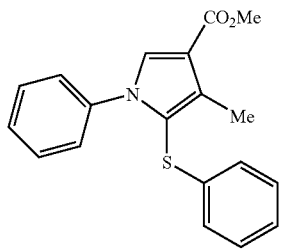

To a solution of methyl 4-methyl-1-phenyl-1H-pyrrole-3-carboxylate (540 mg) in tetrahydrofuran (10 mL) were added N-iodosuccinimide (677 mg) and thiophenol (0.257 mL), and the mixture was stirred at room temperature for 2 days. Saturated aqueous sodium thiosulfate solution (10 mL) was added to the reaction mixture, and the mixture was extracted with ethyl acetate. The extract was washed with saturated brine, dried over anhydrous sodium sulfate, and concentrated under reduced pressure to give the title compound as a pale-yellow oil (yield 812 mg, about 100%).

¹H-NMR (CDCl₃) δ: 2.45 (3H, s), 3.85 (3H, s), 6.87 (2H, dd, J=7.8, 1.6 Hz), 7.05-7.40 (8H, m), 7.66 (1H, s).

Reference Example 4

Methyl 4-methyl-1-phenyl-5-(phenylsulfonyl)-1H-pyrrole-3-carboxylate

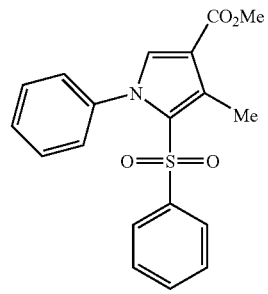

To a solution of methyl 4-methyl-1-phenyl-5-(phenylthio)-1H-pyrrole-3-carboxylate (812 mg) in ethyl acetate (15 mL) was added 3-chloroperbenzoic acid (1.08 g), and the mixture was stirred at room temperature for 18 hr. Furthermore, 3-chloroperbenzoic acid (1.08 g) was added, and the mixture was stirred at room temperature for 1 hr. Saturated aqueous sodium hydrogen carbonate solution was added to the reaction mixture, and the mixture was extracted with ethyl acetate. The extract was washed with saturated brine, dried over anhydrous sodium sulfate, and concentrated under reduced pressure. The residue was purified by silica gel column chromatography (eluent:hexane-ethyl acetate=9:1→2:1) to give the title compound as a pale-yellow solid (yield 414 mg, 46%).

¹H-NMR (CDCl₃) δ: 2.82 (3H, s), 3.81 (3H, s), 7.00-7.10 (2H, m), 7.20-7.60 (9H, m).

Reference Example 5

4-methyl-1-phenyl-5-(phenylsulfonyl)-1H-pyrrole-3-carbaldehyde

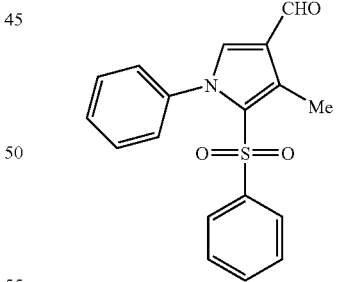

A solution of methyl 4-methyl-1-phenyl-5-(phenylsulfonyl)-1H-pyrrole-3-carboxylate (410 mg) in tetrahydrofuran (10 mL) was cooled to −78° C., and 1.5 mol/L toluene solution of diisobutylaluminum hydride (2.3 mL) was added dropwise. After the completion of the dropwise addition, the mixture was stirred at room temperature for 30 min. Saturated brine was added, and the mixture was stirred at room temperature for 30 min. The reaction mixture was filtered through celite, and the mixture was extracted with ethyl acetate. The extract was washed with saturated brine, dried over anhydrous sodium sulfate, and concentrated under reduced pressure. A solution of the residue in acetonitrile (10 mL) was cooled to 0° C., tetra-n-propylammonium perruthenate (40 mg), N-methylmorpholine N-oxide (269 mg) and molecular sieves 4A powder (1.0 g) were added, and the mixture was stirred at room temperature for 2.5 hr. The reaction mixture was concentrated under reduced pressure, and the residue was suspended in ethyl acetate and filtered through celite. The filtrate was concentrated under reduced pressure, and the residue was purified by silica gel column chromatography (eluent:hexane-ethyl acetate=9:1→2:1) to give the title compound as a pale-yellow oil (yield 170 mg, 45%).

$^1$H-NMR (CDCl$_3$) δ: 2.85 (3H, s), 7.04 (2H, d, J=8.0 Hz), 7.20-7.60 (9H, m), 9.94 (1H, s).

Reference Example 6

2-nitro-1-phenylpropan-1-ol

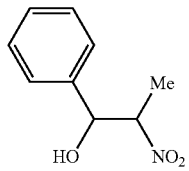

To a solution of benzaldehyde (20.0 g) and nitroethane (28.4 g) in tetrahydrofuran (50 mL) and tert-butanol (50 mL) was added potassium tert-butoxide (1.27 g) under ice-cooling, and the mixture was stirred at room temperature for 16 hr. Water was added to the reaction mixture, and the mixture was extracted with diethyl ether. The extract was washed with saturated aqueous sodium hydrogen carbonate solution and saturated brine, dried over anhydrous magnesium sulfate, and concentrated under reduced pressure. The residue was purified by silica gel column chromatography (eluent:hexane-ethyl acetate=10:1) to give the title compound as a blue oil (yield 32.0 g, 93%).

$^1$H-NMR (CDCl$_3$) δ: 1.23-1.34 (3H, m), 2.56-2.70 (1H, m), 4.68-4.80 (1H, m), 5.01-5.42 (1H, m), 7.32-7.41 (5H, m).

Reference Example 7

2-nitro-1-phenylpropyl Acetate

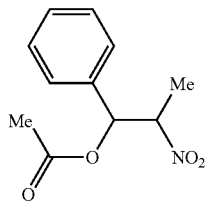

To a solution of 2-nitro-1-phenylpropan-1-ol (32 g) and acetic anhydride (22 mL) in diethyl ether (300 mL) was added 4-dimethylaminopyridine (0.61 g) under ice-cooling, and the mixture was stirred at room temperature for 1 hr. Methanol was added to the reaction mixture, and the mixture was further stirred for 30 min and concentrated under reduced pressure. Water was added to the residue, and the mixture was extracted with ethyl acetate. The extract was washed with saturated aqueous sodium hydrogen carbonate solution, water and saturated brine, dried over anhydrous sodium sulfate, and concentrated under reduced pressure to give the title compound as a yellow oil (yield 34 g, 86%).

$^1$H-NMR (CDCl$_3$) δ: 1.33-1.58 (3H, m), 2.01-2.15 (3H, m), 4.77-4.99 (1H, m), 6.03-6.35 (1H, m), 7.30-7.43 (5H, m).

Reference Example 8

4-methyl-2-[(4-methylphenyl)sulfonyl]-3-phenyl-1H-pyrrole

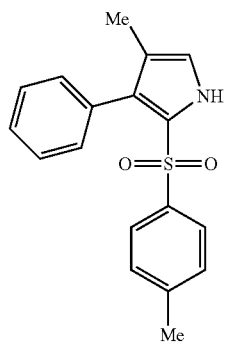

To a solution of p-toluenesulfonylmethyl isocyanide (6.1 g) and 1,1,3,3-tetramethylguanidine (8.3 mL) in tetrahydrofuran (18 mL) and isopropyl alcohol (18 mL) was added dropwise a solution of 2-nitro-1-phenylpropyl acetate (7.0 g) in tetrahydrofuran (3 mL) and isopropyl alcohol (3 mL), and the mixture was stirred at room temperature for 4 hr. Water was added to the reaction mixture, and the mixture was extracted with a mixed solvent of ethyl acetate and tetrahydrofuran. The extract was washed with water and saturated brine, dried over anhydrous magnesium sulfate, and concentrated under reduced pressure. The residue was recrystallized from ethyl acetate-hexane to give the title compound as a white solid (yield 6.1 g, 63%).

$^1$H-NMR (CDCl$_3$) δ: 1.92 (3H, s), 2.32 (3H, s), 6.78-6.80 (1H, m), 7.03-7.07 (2H, m), 7.17-7.22 (2H, m), 7.26-7.37 (5H, m), 9.09 (1H, brs).

Reference Example 9

3-methyl-5-[(4-methylphenyl)sulfonyl]-4-phenyl-1H-pyrrole-2-carbaldehyde

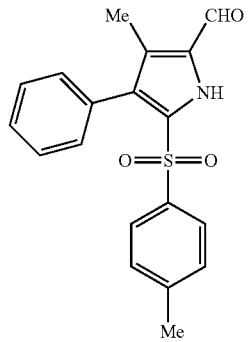

4-Methyl-2-[(4-methylphenyl)sulfonyl]-3-phenyl-1H-pyrrole (374 mg) and (chloromethylene)dimethylammonium chloride (872 mg) were stirred at 60° C. for 16 hr in a mixed solvent of tetrahydrofuran (10 mL) and acetonitrile (5 mL). The reaction mixture was cooled to room temperature, saturated aqueous sodium hydrogen carbonate solution was added, and the mixture was extracted with ethyl acetate. The extract was washed with saturated aqueous sodium hydrogen carbonate solution, water and saturated brine in this order, dried over anhydrous magnesium sulfate, and concentrated under reduced pressure. The residue was purified by silica gel column chromatography (eluent:hexane-ethyl acetate=4:1) to give the title compound as a pale-yellow solid (yield 187 mg, 46%).
$^1$H-NMR (CDCl$_3$) δ: 2.18 (3H, s), 2.34 (3H, s), 7.07-7.16 (4H, m), 7.26-7.29 (2H, m), 7.34-7.41 (3H, m), 9.79 (1H, brs), 9.84 (1H, s).

Reference Example 10

1-[(4-methylphenyl)sulfonyl]-2-phenyl-1H-imidazole-4-carbaldehyde

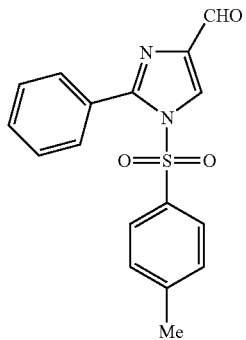

To a solution of 2-phenyl-1H-imidazole-4-carbaldehyde (1.73 g) in N,N-dimethylformamide (35 mL) was added sodium hydride (60% in oil, 483 mg) at room temperature, and the mixture was stirred for 1 hr. 4-Methylphenylsulfonyl chloride (1.92 g) was added, and the mixture was stirred at 50° C. for 30 min. The reaction mixture was cooled, water was added, and the mixture was extracted with ethyl acetate. The extract was washed with water, 1 mol/L hydrochloric acid and saturated aqueous sodium hydrogen carbonate solution, dried over anhydrous magnesium sulfate, and concentrated under reduced pressure. The residue was purified by silica gel column chromatography (eluent:hexane-ethyl acetate=9:1→7:3), and crystallized from diisopropyl ether to give the title compound as colorless crystals (yield 1.95 g, 60%).
$^1$H-NMR (CDCl$_3$) δ: 2.39 (3H, s), 7.15 (2H, d, J=8.2 Hz), 7.28 (2H, d, J=8.2 Hz), 7.37-7.42 (4H, m), 7.49-7.54 (1H, m), 8.29 (1H, s), 9.93 (1H, s).

Reference Example 11

1-(mesitylsulfonyl)-2-phenyl-1H-imidazole-4-carbaldehyde

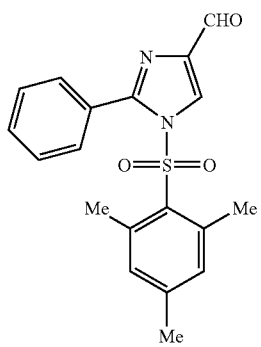

To a solution of 2-phenyl-1H-imidazole-4-carbaldehyde (1.73 g) in N,N-dimethylformamide (30 mL) was added sodium hydride (60% in oil, 523 mg) at room temperature, and the mixture was stirred for 1 hr. Mesitylsulfonyl chloride (2.42 g) was added, and the mixture was stirred for 1 hr. Water was added to the reaction mixture, and the mixture was extracted with ethyl acetate. The extract was washed with saturated aqueous sodium hydrogen carbonate solution, 3% aqueous potassium hydrogensulfate solution and saturated brine, dried over anhydrous magnesium sulfate, and concentrated under reduced pressure. The residue was purified by silica gel column chromatography (eluent:hexane-ethyl acetate=7:3→3:2) to give the title compound as a pale-yellow oil (yield 1.76 g, 49%).
$^1$H-NMR (CDCl$_3$) δ: 2.17 (6H, s), 2.26 (3H, s), 6.78 (2H, s), 7.15-7.23 (4H, m), 7.34-7.38 (1H, m), 8.33 (1H, s), 9.96 (1H, s).

Reference Example 12

2-phenyl-1-(pyridin-3-ylsulfonyl)-1H-imidazole-4-carbaldehyde

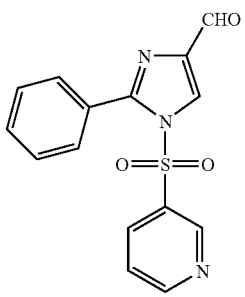

To a solution of 2-phenyl-1H-imidazole-4-carbaldehyde (1.00 g) in tetrahydrofuran (50 mL) was added sodium hydride (60% in oil, 697 mg) at room temperature, and the mixture was stirred for 30 min. 15-Crown-5 (3.84 g) was added dropwise, and the mixture was further stirred for 10 min. 3-Pyridylsulfonyl chloride hydrochloride (1.62 g) was added to the reaction mixture, and the mixture was stirred for 2 hr. Saturated aqueous sodium hydrogen carbonate solution was added, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=3:2→42:3), and the obtained oil was crystallized from diisopropyl ether to give the title compound as colorless crystals (yield 754 mg, 41%).
$^1$H-NMR (CDCl$_3$) δ: 7.29-7.33 (1H, m), 7.37-7.45 (4H, m), 7.53-7.64 (2H, m), 8.33 (1H, s), 8.56 (1H, d, J=2.4 Hz), 8.79 (1H, dd, J=4.9, 1.5 Hz), 9.95 (1H, s).

Reference Example 13

1-[(3-methoxyphenyl)sulfonyl]-2-phenyl-1H-imidazole-4-carbaldehyde

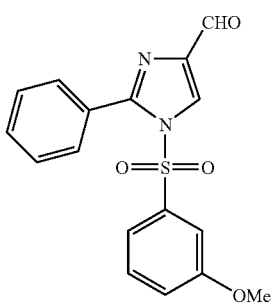

To a solution of 2-phenyl-1H-imidazole-4-carbaldehyde (520 mg) in tetrahydrofuran (100 mL) was added sodium hydride (60% in oil, 182 mg) at room temperature, and the mixture was stirred for 30 min. 3-Methoxybenzenesulfonyl chloride (750 mg) was added to the reaction mixture, and the mixture was stirred for 1.5 hr. Water was added, and the mixture was extracted with ethyl acetate. The extract was washed with saturated brine, dried over anhydrous magnesium sulfate, and concentrated under reduced pressure. The residue was crystallized from diethyl ether to give the title compound as colorless crystals (yield 894 mg, 87%).

$^1$H-NMR (CDCl$_3$) δ: 3.66 (3H, s), 6.81-6.82 (1H, m), 7.01-7.05 (1H, m), 7.08-7.12 (1H, m), 7.25-7.31 (1H, m), 7.37-7.44 (4H, m), 7.49-7.54 (1H, m), 8.30 (1H, s), 9.94 (1H, s).

Reference Example 14

1-[(2,6-difluorophenyl)sulfonyl]-2-phenyl-1H-imidazole-4-carbaldehyde

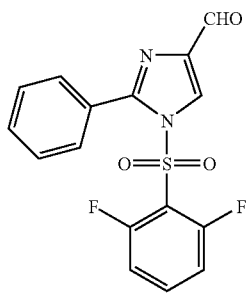

To a solution of 2-phenyl-1H-imidazole-4-carbaldehyde (1.00 g) in tetrahydrofuran (70 mL) was added sodium hydride (60% in oil, 348 mg) at room temperature, and the mixture was stirred for 30 min. 2,6-Difluorobenzenesulfonyl chloride (1.36 g) was added to the reaction mixture, and the mixture was stirred for 1.5 hr. Water was added, and the mixture was extracted with ethyl acetate. The extract was washed with saturated brine, dried over anhydrous magnesium sulfate, and concentrated under reduced pressure. The residue was crystallized from diethyl ether to give the title compound as colorless crystals (yield 1.36 g, 67%).

$^1$H-NMR (CDCl$_3$) δ: 6.82-6.91 (2H, m), 7.27-7.46 (5H, m), 7.51-7.60 (1H, m), 8.38 (1H, s), 9.98 (1H, s).

Reference Example 15

1-(1-benzothien-2-ylsulfonyl)-2-phenyl-1H-imidazole-4-carbaldehyde

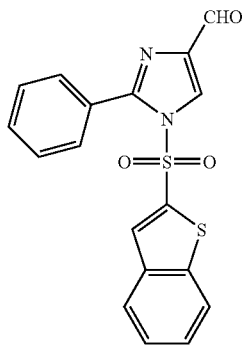

To a solution of 2-phenyl-1H-imidazole-4-carbaldehyde (700 mg) in tetrahydrofuran (70 mL) was added sodium hydride (60% in oil, 244 mg), and the mixture was stirred for 30 min. 1-Benzothiophene-2-sulfonyl chloride (1.04 g) was added to the reaction mixture, and the mixture was stirred for 1.5 hr. Water was added, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=7:3) to give the title compound as a colorless oil (yield 1.25 g, 83%).

$^1$H-NMR (CDCl$_3$) δ: 7.33-8.08 (10H, m), 8.31 (1H, s), 9.94 (1H, s).

Reference Example 16

Ethyl 1-(4-nitrophenyl)-2-[(4-nitrophenyl)thio]-1H-imidazole-4-carboxylate

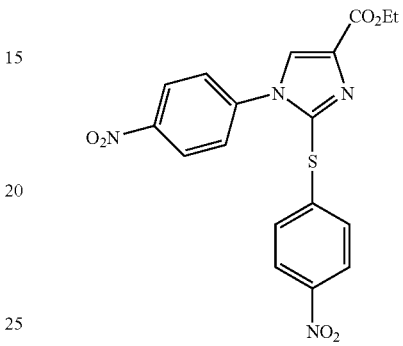

Ethyl 2-mercapto-1H-imidazole-4-carboxylate (1.00 g), 1-fluoro-4-nitrobenzene (2.05 g) and anhydrous potassium carbonate (4.00 g) were mixed in N,N-dimethylformamide (30 mL), and the mixture was stirred at 100° C. for 4 hr. The reaction mixture was cooled, water was added, and the mixture was extracted with ethyl acetate. The extract was washed with saturated brine, dried over anhydrous magnesium sulfate, and concentrated under reduced pressure. Diisopropyl ether was added to the residue and the resulting crystals were collected by filtration to give the title compound as pale-yellow crystals (yield 2.06 g, 86%). $^1$H-NMR (CDCl$_3$) δ: 1.43 (3H, t, J=7.2 Hz), 4.46 (2H, q, J=7.2 Hz), 7.21-7.26 (2H, m), 7.46-7.51 (2H, m), 8.01 (1H, s) 8.07-8.11 (2H, m), 8.31-8.36 (2H, m).

Reference Example 17

Ethyl 1-(4-aminophenyl)-2-[(4-aminophenyl)thio]-1H-imidazole-4-carboxylate

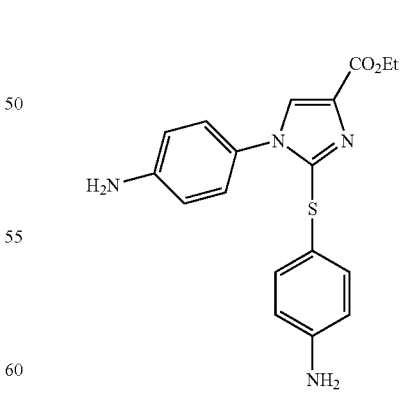

Ethyl 1-(4-nitrophenyl)-2-[(4-nitrophenyl)thio]-1H-imidazole-4-carboxylate (3.00 g) was suspended in ethanol (120 mL), iron powder (4.05 g), anhydrous calcium chloride (0.81 g) and water (20 mL) were added, and the mixture was heated under reflux for 4 hr. The reaction mixture was allowed to cool, and filtered. Saturated aqueous sodium hydrogen carbonate solution was added to the obtained filtrate, and the mixture was extracted with ethyl acetate. The extract was washed with saturated brine, dried over anhydrous magnesium sulfate, and concentrated under reduced pressure. Methanol (30 mL) was added to the residue and the resulting crystals were collected by filtration to give the title compound as pale-yellow crystals (yield 2.00 g, 78%).

$^1$H-NMR (DMSO-$d_6$) δ: 1.25 (3H, t, J=7.1 Hz), 4.21 (2H, q, J=7.1 Hz), 5.40 (2H, s), 5.49 (2H, s), 6.46-6.51 (2H, m), 6.59-6.64 (2H, m), 6.93-6.97 (2H, m), 6.99-7.04 (2H, m), 7.95 (1H, s).

Reference Example 18

Ethyl 1-phenyl-2-(phenylthio)-1H-imidazole-4-carboxylate

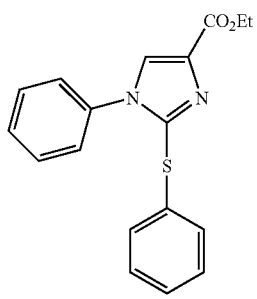

Ethyl 1-(4-aminophenyl)-2-[(4-aminophenyl)thio]-1H-imidazole-4-carboxylate (1.90 g) was dissolved in concentrated hydrochloric acid (30 mL), and a solution of sodium nitrite (1.00 g) in water (5 mL) was added dropwise at 5-10° C. The mixture was stirred at the same temperature for 1 hr, and the obtained reaction mixture was added dropwise to 50% aqueous hypophosphorous acid solution (30 mL) by small portions. The mixture was stirred at room temperature for 3 hr, and extracted with ethyl acetate. The extract was washed with saturated aqueous sodium hydrogen carbonate solution, water and saturated brine in this order, dried over anhydrous magnesium sulfate, and concentrated under reduced pressure to give the title compound as a yellow oil (yield 1.17 g, 67%).

$^1$H-NMR (CDCl$_3$) δ: 1.40 (3H, t, J=7.1 Hz), 4.41 (2H, q, J=7.1 Hz), 7.08-7.17 (7H, m), 7.35-7.43 (3H, m), 7.85 (1H, s).

Reference Example 19

[1-phenyl-2-(phenylthio)-1H-imidazol-4-yl]methanol

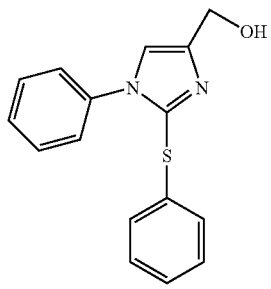

A solution (30 mL) of ethyl 1-phenyl-2-(phenylthio)-1H-imidazole-4-carboxylate (1.17 g) in tetrahydrofuran was cooled to −70° C., and a 1.5 mol/L solution (12 mL) of diisobutylaluminum hydride in toluene was added dropwise by small portions. The reaction mixture was stirred at 0° C. for 4 hr, water was added, and the mixture was stirred for 30 min. To the obtained gel-like substance was added tetrahydrofuran, the mixture was filtered, and the filtrate was concentrated under reduced pressure. A mixed solvent of ethyl acetate-diisopropyl ether (1:1) was added to the residue and the resulting unsoluble crystals were collected by filtration to give the title compound as pale-yellow crystals (yield 797 mg, 78%).

$^1$H-NMR (CDCl$_3$) δ: 2.59 (1H, br), 4.69 (2H, s), 7.08-7.24 (8H, m), 7.37-7.41 (3H, m).

Reference Example 20

1-phenyl-2-(phenylthio)-1H-imidazole-4-carbaldehyde

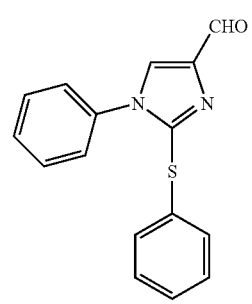

To a solution of [1-phenyl-2-(phenylthio)-1H-imidazol-4-yl]methanol (740 mg) in acetonitrile (50 mL) were added tetra-n-propylammonium perruthenate (185 mg), N-methylmorpholine N-oxide (1.42 g) and molecular sieves 4A powder (5 g), and the mixture was stirred at room temperature for 2 hr. The reaction mixture was filtered through celite, and the filtrate was concentrated under reduced pressure. The residue was purified by silica gel column chromatography (eluent: hexane-ethyl acetate=3:2) to give the title compound as a pale-yellow oil (yield 400 mg, 54%).

$^1$H-NMR (CDCl$_3$) δ: 7.18-7.25 (7H, m), 7.41-7.49 (3H, m), 7.85 (1H, s), 9.96 (1H, s).

Reference Example 21

N-methyl-1-[1-phenyl-2-(phenylthio)-1H-imidazol-4-yl]methanamine Dihydrochloride

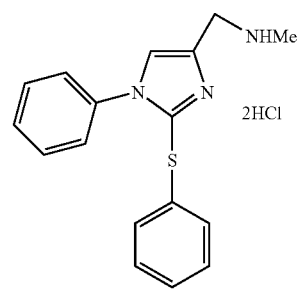

To a solution of 1-phenyl-2-(phenylthio)-1H-imidazole-4-carbaldehyde (400 mg) in methanol (10 mL) was added 40% methylamine methanol solution (554 mg) at room temperature, and the mixture was stirred for 30 min. Sodium borohydride (108 mg) was added, and the mixture was stirred for 15 min. Water was added, and the mixture was further stirred for 10 min. The reaction mixture was alkalified with saturated aqueous sodium hydrogen carbonate solution, and extracted with ethyl acetate. The extract was washed with saturated brine, dried over anhydrous magnesium sulfate, and concentrated under reduced pressure. The residue was purified by basic silica gel column chromatography (eluent:ethyl acetate), and dissolved in methanol (5 mL). 4 mol/L Hydrogen chloride-ethyl acetate solution (1 mL) was added, and the mixture was concentrated under reduced pressure. The residue was crystallized from tetrahydrofuran to give the title compound as colorless crystals (yield 347 mg, 66%).

$^1$H-NMR (DMSO-$d_6$) δ: 2.58 (3H, t, J=5.5 Hz), 4.11 (2H, t, J=5.5 Hz), 7.07-7.10 (2H, m), 7.19-7.39 (5H, m), 7.47-7.54 (3H, m) 7.87 (1H, s), 8.75 (1H, br), 9.40 (2H, br).

Reference Example 22

Ethyl 2,4-dioxo-4-phenylbutanoate

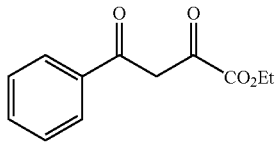

Sodium hydride (60% in oil, 4.0 g) was washed with hexane, suspended in N,N-dimethylformamide (30 mL), and a solution of acetophenone (10 g) and diethyl oxalate (115 g) in N,N-dimethylformamide (50 mL) was added. The reaction solution was stirred at room temperature, at 50° C. for 30 min, and concentrated under reduced pressure. 6 mol/L Hydrochloric acid was added to the residue, and the mixture was extracted with ethyl acetate. The extract was washed with saturated brine, dried over anhydrous sodium sulfate, and concentrated under reduced pressure to give the title compound as a colorless oil (yield 16 g, about 100%).

$^1$H-NMR (CDCl$_3$) δ: 1.42 (3H, t, J=8.8 Hz), 4.40 (2H, q, J=8.8 Hz), 7.09 (1H, s), 7.40-7.70 (3H, m), 7.95-8.10 (2H, m), 1H not detected.

Reference Example 23

Ethyl 5-phenyl-1H-pyrazole-3-carboxylate

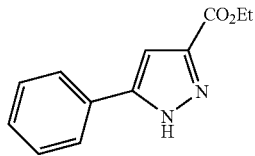

To a solution of ethyl 2,4-dioxo-4-phenylbutanoate (16.0 g) in ethanol (150 mL) was added hydrazine monohydrate (4.0 mL), and the mixture was heated under reflux for 3 hr. The reaction mixture was concentrated under reduced pressure, and the residue was crystallized from diisopropyl ether to give the title compound as a pale-brown solid (yield 12.0 g, 67%).

$^1$H-NMR (CDCl$_3$) δ: 1.41 (3H, t, J=7.4 Hz), 4.41 (2H, q, J=7.4 Hz), 4.80-6.50 (1H, brs), 7.12 (1H, s), 7.30-7.50 (3H, m), 7.79 (2H, d, J=7.9 Hz).

Reference Example 24

Ethyl 1-[(4-methylphenyl)sulfonyl]-5-phenyl-1H-pyrazole-3-carboxylate

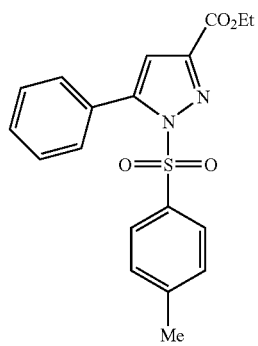

Sodium hydride (60% in oil, 612 mg) was washed with hexane, suspended in N,N-dimethylformamide solution (5 mL), and a solution of ethyl 5-phenyl-1H-pyrazole-3-carboxylate (3.0 g) in N,N-dimethylformamide (10 mL) was added dropwise. After the completion of the dropwise addition, the reaction mixture was stirred at room temperature for 30 min, and added dropwise to an ice-cooled solution of p-toluenesulfonyl chloride (3.16 g) in N,N-dimethylformamide (10 mL). After the completion of the dropwise addition, the reaction mixture was stirred at room temperature for 1 hr, and concentrated under reduced pressure. Water was added to the residue, and the mixture was extracted with ethyl acetate. The extract was washed with saturated brine, dried over anhydrous sodium sulfate, and concentrated under reduced pressure. The residue was purified by basic silica gel column chromatography (eluent:hexane-ethyl acetate=9:1→1:1) to give the title compound as a colorless solid (yield 1.037 g, 20%).

$^1$H-NMR (CDCl$_3$) δ: 1.42 (3H, t, J=7.4 Hz), 2.43 (3H, s), 4.43 (2H, q, J=7.4 Hz), 7.03 (1H, s), 7.30-7.50 (5H, m), 7.75-7.85 (2H, m), 8.07 (2H, d, J=8.4 Hz).

Reference Example 25

1-[(4-methylphenyl)sulfonyl]-5-phenyl-1H-pyrazole-3-carbaldehyde

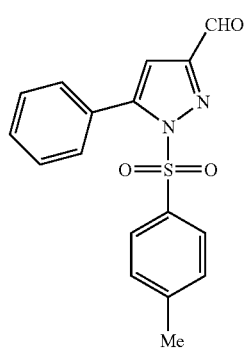

A solution of ethyl 1-[(4-methylphenyl)sulfonyl]-5-phenyl-1H-pyrazole-3-carboxylate (700 mg) in tetrahydrofuran (10 mL) was cooled to −78° C., and a 1.5 mol/L solution (3.8 mL) of diisobutylaluminum hydride in toluene was added dropwise. After the completion of the dropwise addition, the mixture was stirred at −78° C. for 30 min. 1 mol/L Hydrochloric acid was added, and the mixture was extracted with ethyl acetate. The extract was washed with saturated brine, dried over anhydrous sodium sulfate, and concentrated under reduced pressure. To a solution of the residue in acetonitrile (15 mL) were added tetra-n-propylammonium perruthenate (66 mg), N-methylmorpholine N-oxide (442 mg) and molecular sieves 4A powder (1.0 g), and the mixture was stirred at room temperature for 1 hr. The reaction mixture was concentrated under reduced pressure, and the residue was suspended in ethyl acetate and filtered through celite. The filtrate was concentrated under reduced pressure, and the residue was purified by silica gel column chromatography (eluent:hexane-ethyl acetate=9:1→2:1) to give the title compound as a pale-yellow solid (yield 224 mg, 36%).

$^1$H-NMR (CDCl$_3$) δ: 2.42 (3H, s), 6.72 (1H, s), 7.20-7.55 (7H, m), 7.59 (2H, d, J=8.4 Hz), 10.02 (1H, s).

Reference Example 26

1-phenyl-2-(phenylthio)ethanone

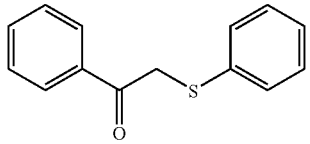

To a suspension of 2-bromoacetophenone (10 g) and potassium carbonate (7.1 g) in ethanol (150 mL) was added thiophenol (5.2 mL) under ice-cooling, and the mixture was stirred at room temperature for 12 hr. The insoluble material was filtered off, and the filtrate was concentrated under reduced pressure. Water was added to the residue, and the mixture was extracted with ethyl acetate. The extract was washed with saturated aqueous sodium hydrogen carbonate solution, water and saturated brine in this order, dried over anhydrous magnesium sulfate, and concentrated under reduced pressure. The residue was purified by silica gel column chromatography (eluent:hexane-ethyl acetate=15:1) to give the title compound as yellow crystals (yield 11 g, 98%).

$^1$H-NMR (CDCl$_3$) δ: 4.28 (2H, s), 7.20-7.32 (3H, m), 7.37-7.41 (1H, m), 7.44-7.50 (4H, m), 7.56-7.62 (1H, m), 7.93-7.97 (1H, m).

Reference Example 27

2-bromo-1-phenyl-2-(phenylthio)ethanone

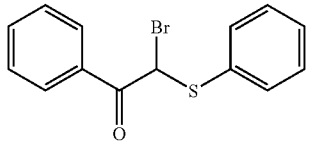

To a solution of 1-phenyl-2-(phenylthio)ethanone (2.1 g) in acetic acid (20 mL) was added bromine (0.5 mL), and the mixture was stirred at room temperature for 1 hr. The reaction mixture was concentrated under reduced pressure, water was added to the residue, and the mixture was extracted with ethyl acetate. The extract was washed with saturated aqueous sodium hydrogen carbonate solution, water and saturated brine, dried over anhydrous magnesium sulfate, and concentrated under reduced pressure to give the title compound as a yellow oil (yield 2.9 g, about 100%).

$^1$H-NMR (CDCl$_3$) δ: 6.48 (1H, s), 7.40-7.44 (5H, m), 7.48-7.53 (3H, m), 8.04-8.07 (2H, m).

Reference Example 28

(1,3-dioxo-1,3-dihydro-2H-isoindol-2-yl)acetonitrile

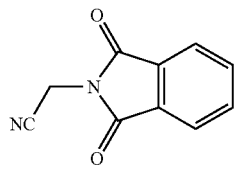

To a solution of bromoacetonitrile (22 g) in N,N-dimethylformamide (200 mL) was added potassium phthalimide (34 g) under ice-cooling, and the mixture was stirred at room temperature for 3 hr. Water was added to the reaction mixture, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was recrystallized from ethanol to give the title compound as white crystals (yield 27 g, 80%).

$^1$H-NMR (CDCl$_3$) δ: 4.59 (2H, s), 7.79-7.85 (2H, m), 7.90-7.97 (2H, m).

Reference Example 29

2-(1,3-dioxo-1,3-dihydro-2H-isoindol-2-yl)ethanethioamide

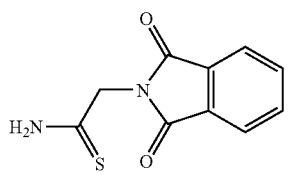

To a mixture of (1,3-dioxo-1,3-dihydro-2H-isoindol-2-yl)acetonitrile (15 g), 4 mol/L hydrogen chloride-ethyl acetate solution (40 mL) and tetrahydrofuran (50 mL) was added O,O-diethyldithiophosphate (15 mL), and the mixture was stirred at room temperature for 5 hr. Water was added to the reaction mixture, and the mixture was extracted with ethyl acetate and tetrahydrofuran. The extract was washed twice with water, and then washed with saturated brine and saturated aqueous sodium hydrogen carbonate solution, dried over anhydrous magnesium sulfate, and concentrated under reduced pressure. The residue was recrystallized from ethanol to give the title compound as white crystals (yield 9.0 g, 51%).

¹H-NMR (CDCl₃) δ: 4.69 (2H, s), 7.25 (1H, brs), 7.47 (1H, brs), 7.75-7.79 (2H, m), 7.88-7.92 (2H, s).

Reference Example 30

2-{[4-phenyl-5-(phenylthio)-1,3-thiazol-2-yl]methyl}-1H-isoindole-1,3(2H)-dione

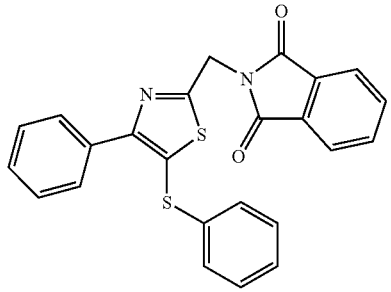

To a solution of 2-bromo-1-phenyl-2-(phenylthio)ethanone (3.2 g) in N,N-dimethylformamide (25 mL) was added 2-(1,3-dioxo-1,3-dihydro-2H-isoindol-2-yl)ethanethioamide (2.3 g), and the mixture was stirred at room temperature for 3 hr. Saturated aqueous sodium hydrogen carbonate solution was added to the reaction mixture, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was recrystallized from ethyl acetate-hexane to give the title compound as white crystals (yield 3.0 g, 71%).

¹H-NMR (CDCl₃) δ: 5.19 (2H, s), 7.15-7.28 (5H, m), 7.33-7.40 (3H, m), 7.75-7.79 (2H, m), 7.88-7.93 (4H, m).

Reference Example 31

1-[4-phenyl-5-(phenylthio)-1,3-thiazol-2-yl]methanamine

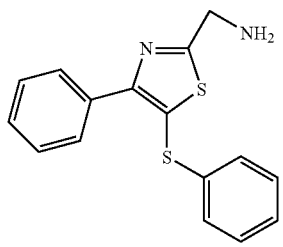

To a suspension of 2-{[4-phenyl-5-(phenylthio)-1,3-thiazol-2-yl]methyl}-1H-isoindole-1,3(2H)-dione (0.53 g) in ethanol (5 mL) was added hydrazine monohydrate (0.1 mL), and the mixture was stirred at 70° C. for 1 hr. The reaction mixture was cooled to room temperature, water was added, and the mixture was extracted with ethyl acetate. The extract was washed with saturated aqueous sodium hydrogen carbonate solution, water and saturated brine, dried over anhydrous magnesium sulfate, and concentrated under reduced pressure to give the title compound as a yellow oil (yield 0.36 g, 97%).

¹H-NMR (CDCl₃) δ: 1.72 (2H, brs), 4.21 (2H, s), 7.16-7.30 (5H, m), 7.35-7.43 (3H, m), 7.88-7.92 (2H, m).

Reference Example 32 tert-butyl {[4-phenyl-5-(phenylthio)-1,3-thiazol-2-yl]methyl}carbamate

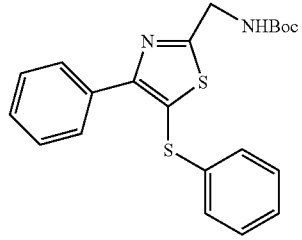

To a solution of 1-[4-phenyl-5-(phenylthio)-1,3-thiazol-2-yl]methanamine (0.36 g) in ethyl acetate (5 mL) was added di-tert-butyl bicarbonate (0.3 mL), and the mixture was stirred at room temperature for 3 hr. Water was added to the reaction mixture, and the mixture was extracted with ethyl acetate. The extract was washed with saturated aqueous sodium hydrogen carbonate solution, water and saturated brine in this order, dried over anhydrous sodium sulfate, and concentrated under reduced pressure. The residue was purified by silica gel column chromatography (eluent:hexane-ethyl acetate=5:1) to give the title compound as a pale-yellow oil (yield 0.40 g, 84%).

¹H-NMR (CDCl₃) δ: 1.47 (9H, s), 4.63 (2H, brd, J=6.3 Hz), 5.27 (1H, brs), 7.16-7.30 (5H, m), 7.32-7.43 (3H, m), 7.87-7.91 (2H, m).

Reference Example 33 tert-butyl methyl{[4-phenyl-5-(phenylthio)-1,3-thiazol-2-yl]methyl}carbamate

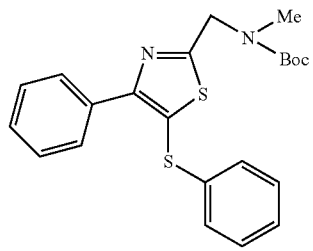

Sodium hydride (60% in oil, 62 mg) was washed twice with hexane, and suspended in N,N-dimethylformamide (10 mL). To the suspension was added a solution of tert-butyl {[4-phenyl-5-(phenylthio)-1,3-thiazol-2-yl]methyl}carbamate (0.40 g) in N,N-dimethylformamide (2 mL) under ice-cooling, and the mixture was stirred at the same temperature for 10 min. To the obtained mixture was added methyl iodide (0.1 mL) under ice-cooling, and the reaction mixture was stirred at room temperature for 10 min. Water was added to the reaction mixture, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was purified by silica gel column chromatography (eluent:hexane-ethyl acetate=5:1) to give the title compound as a pale-yellow oil (yield 0.28 g, 68%).

$^1$H-NMR (CDCl$_3$) δ: 1.46 (9H, brs), 3.01 (3H, brs), 4.64-4.73 (2H, m), 7.19-7.30 (5H, m), 7.36-7.40 (3H, m), 7.89-7.92 (2H, m).

Reference Example 34 tert-butyl methyl{[4-phenyl-5-(phenylsulfonyl)-1,3-thiazol-2-yl]methyl}carbamate

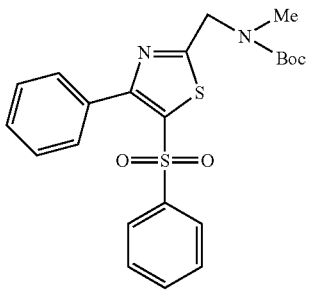

To a solution of tert-butyl methyl{[4-phenyl-5-(phenylthio)-1,3-thiazol-2-yl]methyl}carbamate (0.27 g) in N,N-dimethylformamide (3 mL) was added 3-chloroperbenzoic acid (0.57 g) under ice-cooling, and the mixture was stirred at room temperature for 30 min. Aqueous sodium thiosulfate solution was added to the reaction mixture, and the mixture was extracted with ethyl acetate. The extract was washed with saturated aqueous sodium hydrogen carbonate solution, water and saturated brine in this order, dried over anhydrous magnesium sulfate, and concentrated under reduced pressure. The residue was dissolved in acetic acid (2 mL), 3-chloroperbenzoic acid (0.96 g) was added thereto, and the mixture was stirred at room temperature for 30 min. Aqueous sodium thiosulfate solution was added to the reaction mixture, and the mixture was extracted with ethyl acetate. The extract was washed with saturated aqueous sodium hydrogen carbonate solution, water and saturated brine, dried over anhydrous magnesium sulfate, and concentrated under reduced pressure. The residue was purified by silica gel column chromatography (eluent:hexane-ethyl acetate=2:1) to give the title compound as a pale-yellow oil (yield 0.18 g, 63%).

$^1$H-NMR (CDCl$_3$) δ: 1.49-1.52 (9H, m), 3.01 (3H, s), 4.64-4.70 (2H, m), 7.29-7.57 (10H, m).

Reference Example 35

2-phenyl-1-(2-thienylsulfonyl)-1H-imidazole-4-carbaldehyde

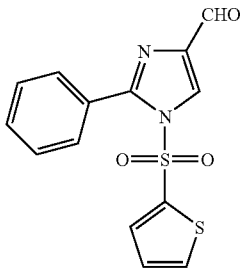

To a solution of 2-phenyl-1H-imidazole-4-carbaldehyde (1.73 g) in tetrahydrofuran (100 mL) was added sodium hydride (60% in oil, 603 mg) at room temperature, and the mixture was stirred for 15 min. Thiophene-2-sulfonyl chloride (2.39 g) was added to the reaction mixture, and the mixture was stirred for 1 hr. Saturated aqueous sodium hydrogen carbonate solution was added, and the mixture was extracted with ethyl acetate. The extract was washed with saturated brine, dried over anhydrous magnesium sulfate, and concentrated under reduced pressure. The residue was purified by silica gel column chromatography (eluent:hexane-ethyl acetate=3:2→2:3) to give the title compound as a colorless oil (yield 750 mg, 23%).

$^1$H-NMR (CDCl$_3$) δ: 6.94 (1H, dd, J=5.0, 4.0 Hz), 7.18 (1H, dd, J=4.0, 1.5 Hz), 7.39-7.56 (5H, m), 7.69 (1H, dd, J=5.0, 1.5 Hz), 8.28 (1H, s), 9.94 (1H, s).

Example 1

N-methyl-1-[4-methyl-1-phenyl-5-(phenylsulfonyl)-1H-pyrrol-3-yl]methanamine Hydrochloride

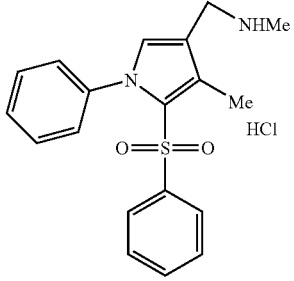

To a solution of 4-methyl-1-phenyl-5-(phenylsulfonyl)-1H-pyrrole-3-carbaldehyde (165 mg) in methanol (5 mL) was added 40% methylamine methanol solution (0.196 mL), and the mixture was stirred at room temperature for 30 min. Sodium borohydride (58 mg) was added to the reaction mixture, and the mixture was stirred at room temperature for 30 min. The reaction mixture was concentrated under reduced pressure, water was added to the residue, and the mixture was extracted with ethyl acetate. The extract was washed with saturated brine, dried over anhydrous sodium sulfate, and concentrated under reduced pressure. The residue was purified by basic silica gel column chromatography (eluent:hexane-ethyl acetate=9:1→0:1). The obtained colorless oil was dissolved in ethyl acetate (5 mL), and 4 mol/L hydrogen chloride-ethyl acetate solution (0.5 mL) was added. The precipitated crystals were collected by filtration, and dried under reduced pressure to give the title compound as a colorless solid (yield 108 mg, 56%).

$^1$H-NMR (DMSO-d$_6$) δ: 2.47 (3H, s), 2.54 (3H, s), 3.98 (2H, s), 7.00-7.10 (2H, m), 7.30-7.70 (9H, m), 8.92 (2H, br).

Example 2

N-methyl-1-{3-methyl-5-[(4-methylphenyl)sulfonyl]-4-phenyl-1H-pyrrol-2-yl}methanamine hydrochloride

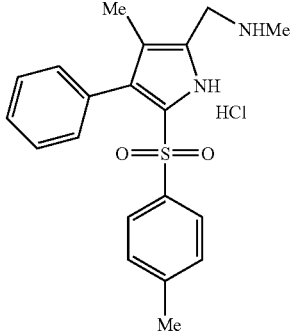

To a solution of 3-methyl-5-[(4-methylphenyl)sulfonyl]-4-phenyl-1H-pyrrole-2-carbaldehyde (134 mg) in tetrahydrofuran (2 mL) were added 40% methylamine methanol solution (0.4 mL) and methanol (2 mL) at room temperature, and the mixture was stirred for 30 min. Sodium borohydride (23.6 mg) was added to the reaction mixture, and the mixture was further stirred at room temperature for 30 min and concentrated under reduced pressure. Saturated aqueous sodium hydrogen carbonate solution was added to the residue, and the mixture was extracted with ethyl acetate. The extract was washed with saturated aqueous sodium hydrogen carbonate solution, water and saturated brine in this order, dried over anhydrous sodium sulfate, and concentrated under reduced pressure. The residue was purified by basic silica gel column chromatography (eluent:ethyl acetate:methanol=20:1) to give a free salt of the title compound (yield 113 mg). To a solution of the obtained free salt in ethyl acetate (2 mL) was added 4 mol/L hydrogen chloride-ethyl acetate solution (2 mL), and the mixture was stirred at room temperature for 15 min. The reaction mixture was concentrated under reduced pressure, and the residue was recrystallized from ethanol to give the title compound as white crystals (yield 32 mg, 21%).

$^1$H-NMR (DMSO-d$_6$) δ: 2.33 (3H, s), 2.57 (3H, s), 3.33 (3H, s), 4.14 (2H, s), 7.07-7.10 (2H, m), 7.25-7.28 (2H, m), 7.34-7.39 (5H, m), 8.87 (2H, brs), 12.20 (1H, brs).

Example 3

N-methyl-1-{1-[(4-methylphenyl)sulfonyl]-2-phenyl-1H-imidazol-4-yl}methanamine 0.5 Oxalate

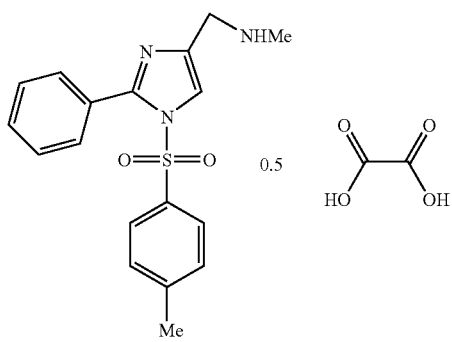

1-[(4-Methylphenyl)sulfonyl]-2-phenyl-1H-imidazole-4-carbaldehyde (1.00 g) was dissolved in methanol (30 mL), 40% methylamine methanol solution (700 mg) was added at room temperature, and the mixture was stirred for 30 min. Sodium borohydride (171 mg) was added at 5-10° C., and the mixture was stirred for 30 min. 1 mol/L Hydrochloric acid was added at the same temperature, and the mixture was further stirred for 30 min. The reaction mixture was alkalified with saturated aqueous sodium hydrogen carbonate solution, and the mixture was extracted with ethyl acetate. The extract was washed with saturated brine, dried over anhydrous magnesium sulfate, and concentrated under reduced pressure. The residue was purified by basic silica gel column chromatography (eluent:hexane-ethyl acetate=1:1→0:1), dissolved in ethyl acetate (10 mL), and crystallized by adding a solution (5 mL) of anhydrous oxalic acid (53 mg) in ethyl acetate to give the title compound as colorless crystals (yield 197 mg, 17%).

$^1$H-NMR (DMSO-d$_6$) δ: 2.37 (3H, s), 2.57 (3H, s), 4.07 (2H, s), 7.32-7.47 (8H, m), 7.53-7.57 (1H, m), 8.00 (1H, s), 2H not detected.

Example 4

1-[1-(mesitylsulfonyl)-2-phenyl-1H-imidazol-4-yl]-N-methylmethanamine 0.5 Oxalate

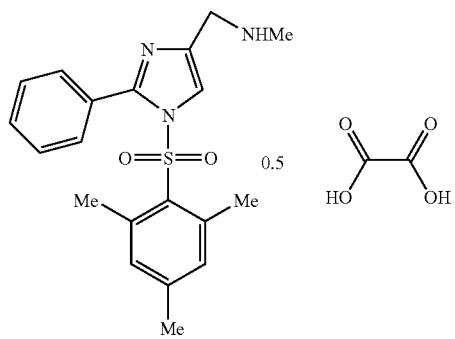

1-(Mesitylsulfonyl)-2-phenyl-1H-imidazole-4-carbaldehyde (2.20 g) was dissolved in methanol (30 mL), 40% methylamine methanol solution (1.45 g) was added at room temperature, and the mixture was stirred for 30 min. Sodium borohydride (353 mg) was added at 5-10° C., and the mixture was stirred for 30 min. 1 mol/L Hydrochloric acid (15 mL) was added at the same temperature, and the mixture was further stirred for 30 min. The reaction mixture was alkalified with saturated aqueous sodium hydrogen carbonate solution, and the mixture was extracted with ethyl acetate. The extract was washed with saturated brine, dried over anhydrous magnesium sulfate, and concentrated under reduced pressure. The residue was purified by basic silica gel column chromatography (eluent:hexane-ethyl acetate=1:1→0:1) to give a free salt of the title compound as a colorless oil (yield 1.47 g). The obtained free salt (0.85 g) was dissolved in ethyl acetate (30 mL), and crystallized by adding a solution of anhydrous oxalic acid (208 mg) in ethyl acetate (30 mL) to give the title compound as colorless crystals (yield 932 mg, 62%).

$^1$H-NMR (DMSO-d$_6$) δ: 2.13 (6H, s), 2.24 (3H, s), 2.59 (3H, s), 4.12 (2H, s), 6.97 (2H, s), 7.07-7.10 (2H, m), 7.25-7.50 (3H, m), 7.99 (1H, s), 2H not detected.

Example 5

N,N-dimethyl-1-{1-[(4-methylphenyl)sulfonyl]-2-phenyl-1H-imidazol-4-yl}methanamine 0.5 Oxalate

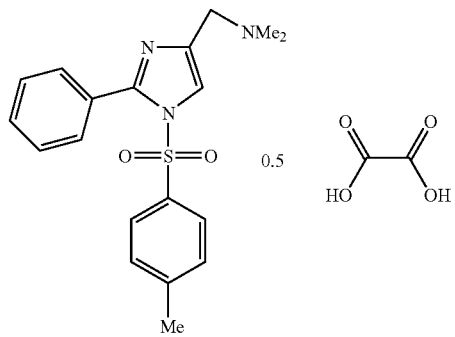

A mixture of 1-[(4-methylphenyl)sulfonyl]-2-phenyl-1H-imidazole-4-carbaldehyde (300 mg), methylammonium chloride (225 mg), molecular sieves 3A (2.0 g) and ethanol (10 mL) was stirred at 60° C. for 1 hr. The reaction mixture was cooled, sodium borohydride (105 mg) was added at 5-10° C., and the mixture was stirred for 30 min. Saturated aqueous sodium hydrogen carbonate was added at the same temperature, and the mixture was extracted with ethyl acetate. The extract was washed with saturated brine, dried over anhydrous magnesium sulfate, and concentrated under reduced pressure. The residue was purified by basic silica gel column chromatography (eluent:hexane-ethyl acetate=2:3→0:1), and crystallized by adding a solution (10 mL) of anhydrous oxalic acid in ethyl acetate to give the title compound as colorless crystals (yield 106 mg, 29%).

$^1$H-NMR (DMSO-d$_6$) δ: 2.37 (3H, s), 2.74 (6H, s), 4.19 (2H, s), 7.32-7.57 (9H, m), 8.06 (1H, s), 2H not detected.

Example 6

N-methyl-1-[2-phenyl-1-(pyridin-3-ylsulfonyl)-1H-imidazol-4-yl]methanamine Fumarate

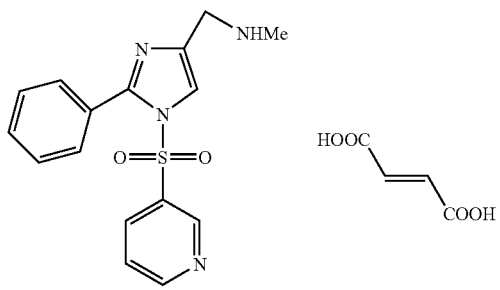

2-Phenyl-1-(pyridin-3-ylsulfonyl)-1H-imidazole-4-carbaldehyde (200 mg) was dissolved in a solution of methylammonium chloride (216 mg) in methanol (10 mL), and the mixture was stirred for 30 min. Sodium triacetoxyborohydride (203 mg) was added, and the mixture was stirred for 5 hr. The reaction mixture was concentrated under reduced pressure at 30° C., saturated aqueous sodium hydrogen carbonate solution was added to the residue, and the mixture was extracted with ethyl acetate (60 mL). The extract was washed with saturated brine, dried over anhydrous magnesium sulfate, and concentrated under reduced pressure. The residue was purified by silica gel column chromatography (eluent: ethyl acetate-methanol=1:0→7:3), dissolved in ethyl acetate (20 mL), and crystallized by adding a solution of anhydrous fumaric acid (75 mg) in methanol (2 mL) to give the title compound as colorless crystals (yield 74 mg, 26%).

$^1$H-NMR (DMSO-d$_6$) δ: 2.47 (3H, s), 3.91 (2H, s), 6.51 (2H, s), 7.31-7.47 (4H, m), 7.52-7.58 (1H, m), 7.59-7.63 (1H, m), 7.93-7.97 (2H, m), 8.61 (1H, d, J=2.2 Hz), 8.89 (1H, dd, J=4.9, 1.5 Hz), 3H not detected.

Example 7

1-{1-[(3-methoxyphenyl)sulfonyl]-2-phenyl-1H-imidazol-4-yl}-N-methylmethanamine fumarate

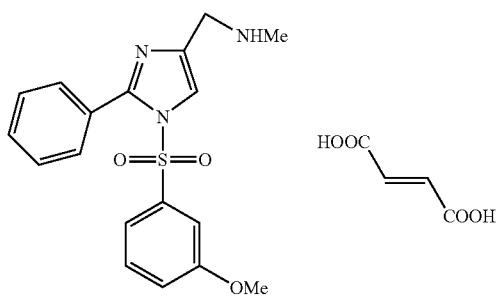

1-[(3-Methoxyphenyl)sulfonyl]-2-phenyl-1H-imidazole-4-carbaldehyde (620 mg) was dissolved in a solution of methylammonium chloride (612 mg) in methanol (40 mL), and the mixture was stirred for 30 min. Sodium triacetoxyborohydride (1.15 g) was added, and the mixture was stirred for 1 hr. The reaction mixture was concentrated under reduced pressure at 30° C., saturated aqueous sodium hydrogen carbonate solution was added to the residue, and the mixture was extracted with ethyl acetate. The extract was washed with saturated brine, dried over anhydrous magnesium sulfate, and concentrated under reduced pressure. The residue was dissolved in ethyl acetate (20 mL), and crystallized by adding a solution of anhydrous fumaric acid (216 mg) in methanol (4 mL) to give the title compound as colorless crystals (yield 317 mg, 37%).

$^1$H-NMR (DMSO-d$_6$) δ: 2.45-2.48 (3H, m), 3.70 (3H, s), 3.88-3.95 (2H, m), 6.50 (2H, s), 6.89-6.90 (1H, m), 7.12-7.15 (1H, m), 7.29-7.56 (7H, m) 7.92-7.97 (1H, m), 3H not detected.

Example 8

1-{1-[(2,6-difluorophenyl)sulfonyl]-2-phenyl-1H-imidazol-4-yl}-N-methylmethanamine fumarate

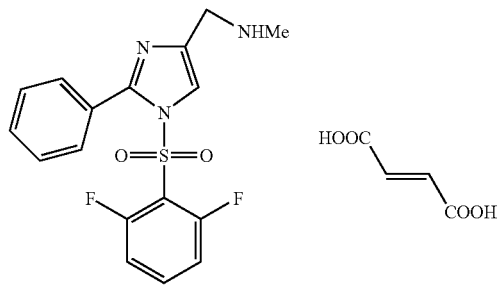

A mixture of 1-[(2,6-difluorophenyl)sulfonyl]-2-phenyl-1H-imidazole-4-carbaldehyde (1.23 g), methylammonium chloride (1.19 g) and methanol (40 mL) was stirred at room temperature for 30 min, sodium triacetoxyborohydride (2.25 g) was added, and the mixture was further stirred for 1 hr. The reaction mixture was concentrated under reduced pressure at 30° C., saturated aqueous sodium hydrogen carbonate solution was added to the residue, and the mixture was extracted with ethyl acetate. The extract was washed with saturated brine, dried over anhydrous magnesium sulfate, and concentrated under reduced pressure. The residue was dissolved in ethyl acetate (40 mL), and crystallized by adding a solution of anhydrous fumaric acid (410 mg) in methanol (4 mL) to give the title compound as colorless crystals (yield 750 mg, 44%).

$^1$H-NMR (DMSO-d$_6$) δ: 2.47 (3H, s), 3.94 (2H, s), 6.50 (2H, s), 7.21-7.38 (6H, m), 7.44-7.50 (1H, m), 7.78-7.88 (1H, m), 7.93 (1H, s), 3H not detected.

Example 9

1-{1-[1-benzothien-2-ylsulfonyl]-2-phenyl-1H-imidazol-4-yl}-N-methylmethanamine Fumarate

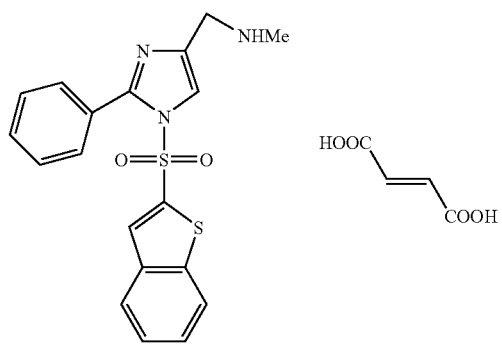

A mixture of 1-(1-benzothien-2-ylsulfonyl)-2-phenyl-1H-imidazole-4-carbaldehyde (1.25 g), methylammonium chloride (1.15 g) and methanol (40 mL) was stirred at room temperature for 30 min, sodium triacetoxyborohydride (2.16 g) was added, and the mixture was further stirred for 1 hr. The reaction mixture was concentrated under reduced pressure at 30° C., saturated aqueous sodium hydrogen carbonate solution was added to the residue, and the mixture was extracted with ethyl acetate. The extract was washed with saturated brine, dried over anhydrous magnesium sulfate, and concentrated under reduced pressure. The residue was purified by basic silica gel column chromatography (eluent:ethyl acetate), dissolved in ethyl acetate (40 mL), and crystallized by adding a solution of anhydrous fumaric acid (394 mg) in methanol (4 mL) to give the title compound as colorless crystals (yield 1.17 g, 69%).

$^1$H-NMR (DMSO-$d_6$) δ: 2.49-2.50 (3H, m), 3.97-3.98 (2H, m), 6.53 (2H, s), 7.44 (4H, d, J=4.3 Hz), 7.52-7.65 (3H, m), 7.97-8.01 (3H, m), 8.11-8.13 (1H, m), 3H not detected.

Example 10

N-methyl-1-[1-phenyl-2-(phenylsulfonyl)-1H-imidazol-4-yl]methanamine dihydrochloride

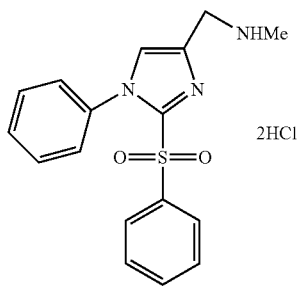

To a solution of N-methyl-1-[1-phenyl-2-(phenylthio)-1H-imidazol-4-yl]methanamine (170 mg) in acetone (40 mL) and water (20 mL) was added an aqueous solution (40 mL) of oxone (2.13 g), and the mixture was stirred at 55° C. for 2 hr. Sodium thiosulfate pentahydrate (1.15 g) was added to the reaction mixture, and the mixture was stirred for 1 hr. Saturated aqueous sodium hydrogen carbonate solution was added, and the mixture was extracted with ethyl acetate. The extract was further extracted twice with a mixed solution of ethyl acetate-tetrahydrofuran (1:1). The combined extract was washed with saturated brine, dried over anhydrous sodium sulfate, and concentrated under reduced pressure. The residue was purified by basic silica gel column chromatography (eluent:ethyl acetate-methanol=7:3→1:0) and dissolved in methanol (5 mL). 4 mol/L Hydrogen chloride-ethyl acetate solution (1 mL) was added and the mixture was concentrated under reduced pressure. The residue was crystallized from tetrahydrofuran to give the title compound as colorless crystals (yield 14 mg, 8%).

$^1$H-NMR (DMSO-$d_6$) δ: 2.58 (3H, s), 4.11 (2H, s), 7.27-7.29 (2H, m), 7.50-7.62 (7H, m), 7.73-7.81 (2H, m), 3H not detected.

Example 11

N-methyl-1-{1-[(4-methylphenyl)sulfonyl]-5-phenyl-1H-pyrazol-3-yl}methanamine Hydrochloride

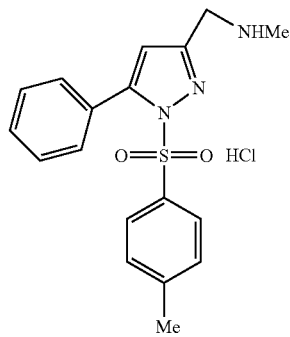

To a solution of 1-[(4-methylphenyl)sulfonyl]-5-phenyl-1H-pyrazole-3-carbaldehyde (220 mg) and methylammonium chloride (455 mg) in methanol (5 mL) was added sodium borohydride (127 mg), and the mixture was stirred at room temperature for 18 hr. The reaction mixture was concentrated under reduced pressure, saturated aqueous sodium hydrogen carbonate solution was added to the residue, and the mixture was extracted with ethyl acetate. The extract was washed with saturated brine, dried over anhydrous sodium sulfate, and concentrated under reduced pressure. The residue was purified by basic silica gel column chromatography (eluent:hexane-ethyl acetate=9:1→0:1). The obtained colorless oil was dissolved in ethyl acetate (5 mL), 4 mol/L hydrogen chloride-ethyl acetate solution (0.5 mL) was added, and the mixture was concentrated under reduced pressure. The residue was recrystallized from ethanol to give the title compound as a colorless solid (yield 70 mg, 27%).

$^1$H-NMR (DMSO-$d_6$) δ: 2.39 (3H, s), 2.55 (3H, s), 4.18 (2H, s), 6.76 (1H, s), 7.30-7.60 (9H, s), 9.35 (2H, br).

Example 12

N-methyl-1-[4-phenyl-5-(phenylsulfonyl)-1,3-thiazol-2-yl]methanamine Hydrochloride

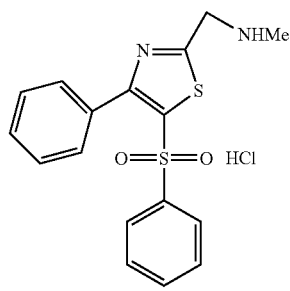

To a solution of tert-butyl methyl{[4-phenyl-5-(phenylsulfonyl)-1,3-thiazol-2-yl]methyl}carbamate (0.18 g) in ethanol (2 mL) was added 4 mol/L hydrogen chloride-ethyl acetate solution (2 mL) at room temperature, and the mixture was stirred for 14 hr. The reaction mixture was concentrated under reduced pressure, and the residue was recrystallized from ethanol to give the title compound as white crystals (yield 80 mg, 53%).

$^1$H-NMR (CDCl$_3$) δ: 2.76 (3H, s), 4.46 (2H, s), 7.26-7.62 (10H, m), 10.31 (2H, brs).

Example 13

N-methyl-1-(2-phenyl-1-(2-thienylsulfonyl)-1H-imidazol-4-yl)methanamine Fumarate

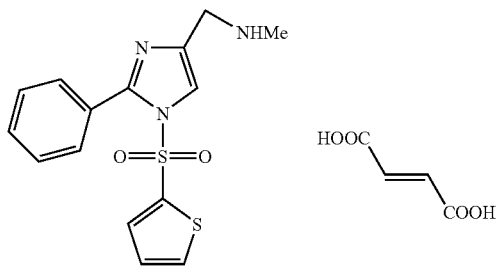

2-Phenyl-1-(2-thienylsulfonyl)-1H-imidazole-4-carbaldehyde (730 mg) was dissolved in a solution of methylammonium chloride (775 mg) in methanol (20 mL), and the mixture was stirred for 30 min. Sodium triacetoxyborohydride (1.46 g) was added, and the mixture was stirred for 1 hr. The reaction mixture was concentrated under reduced pressure at 30° C., saturated aqueous sodium hydrogen carbonate solution was added to the residue, and the mixture was extracted with ethyl acetate. The extract was washed with saturated brine, dried over anhydrous magnesium sulfate, and concentrated under reduced pressure. The residue was purified by basic silica gel column chromatography (eluent:ethyl acetate→ethyl acetate-methanol (97:3)), dissolved in ethyl acetate (10 mL), and crystallized by adding a solution of anhydrous fumaric acid (267 mg) in methanol (2 mL) to give the title compound as colorless crystals (yield 627 mg, 61%).

$^1$H-NMR (DMSO-$d_6$) δ: 2.46 (3H, s), 3.90 (2H, s), 6.50 (2H, s), 7.17 (1H, dd, J=5.0, 4.0 Hz), 7.40-7.58 (6H, m), 7.86 (1H, s), 8.16 (1H, dd, J=5.0, 1.4 Hz), 3H not detected.

Experimental Example 1

Proton Potassium—Adenosine Triphosphatase ($H^+, K^+$-ATPase) Inhibitory Activity Test According to the method [Biochim. Biophys. Acta, 728, 31 (1983)] of Wallmark et al., a gastric mucous membrane microsomal fraction was prepared from the stomach of swine. First, the stomach was removed, washed with tap water, immersed in 3 mol/L brine, and the surface of the mucous membrane was wiped with a paper towel. The gastric mucous membrane was detached, chopped, and homogenized in a 0.25 mol/L saccharose solution (pH 6.8) containing 1 mmol/L EDTA and 10 mmol/L tris-hydrochloric acid using polytron (Kinematica). The obtained homogenate was centrifuged at 20,000×g for 30 min and the supernatant was centrifuged at 100,000×g for 90 min. The precipitate was suspended in 0.25 mol/L saccharose solution, superimposed on a 0.25 mol/L saccharose solution containing 7.5% Ficoll, and centrifuged at 100,000×g for 5 hr. The fraction containing the interface between the both layers was recovered, and centrifugally washed with 0.25 mol/L saccharose solution.

The obtained microsomal fraction was used as a proton, potassium—adenosine triphosphatase standard product.

To 40 μL of a 50 mmol/L HEPES-tris buffer (5 mmol/L magnesium chloride, 10 mmol/L potassium chloride, 10 μmol/L valinomycin, pH=6.5) containing 2.5 μg/mL (based on the protein concentration) of the enzyme standard product was added a test compound (5 μL) dissolved in a 10% aqueous dimethyl sulfoxide solution, and the mixture was incubated at 37° C. for 30 min. The enzyme reaction was started by adding 5 μL of a 2 mmol/L adenosine triphosphate tris salt solution (50 mmol/L HEPES-tris buffer (5 mmol/L magnesium chloride, pH 6.5)). The enzyme reaction was performed at 37° C. for 20 min, and 15 μL of a malachite green solution (0.12% malachite green solution in sulfuric acid (2.5 mol/L), 7.5% ammonium molybdate and 11% Tween 20 were mixed at a ratio of 100:25:2) was added to quench the reaction. After allowing to stand at room temperature for 15 min, the resulting reaction product of inorganic phosphorus with malachite green was calorimetrically determined at a wavelength of 610 nm. In addition, the amount of the inorganic phosphoric acid in the reaction solution free of potassium chloride was measured in the same manner, which was subtracted from the inorganic phosphoric acid amount in the presence of potassium chloride to determine the proton, potassium—adenosine triphosphatase activity. The inhibitory rate (%) was determined from the activity value of the control activity value and the activity values of various concentrations of the test compound, and the 50% inhibitory concentration ($IC_{50}$) of the proton, potassium—adenosine triphosphatase was determined. The results are shown in Table 1.

TABLE 1

| Example compound | $IC_{50}$ (μM) |
|---|---|
| 1 | 0.18 |
| 5 | 0.16 |
| 7 | 0.03 |
| 12 | 0.17 |

INDUSTRIAL APPLICABILITY

Compound (I) of the present invention shows a superior proton pump inhibitory action. Conventional proton pump inhibitors such as omeprazole, lansoprazole and the like form a covalent bond with a cysteine residue of $H^+/K^+$-ATPase, and irreversibly inhibit the enzyme activity. In contrast, compound (I) inhibits proton pump ($H^+/K^+$-ATPase) activity in a reversible and $K^+$ antagonist-like inhibitory manner, and consequently suppresses acid secretion. Therefore, it is sometimes called a potassium-competitive acid blocker (P-CAB), or an acid pump antagonist (APA). Compound (I) rapidly expresses the action and shows the maximum efficacy from the initial administration. Furthermore, it characteristically shows less influence of metabolic polymorphism (variation between patients) and long duration of action. Accordingly, the present invention can provide a clinically useful agent for the prophylaxis or treatment of peptic ulcer (e.g., gastric ulcer, duodenal ulcer, anastomotic ulcer, ulcer caused by non-steroidal anti-inflammatory agent, ulcer due to postoperative stress etc.), Zollinger-Ellison syndrome, gastritis, erosive esophagitis, reflux esophagitis, symptomatic gastroesophageal reflux disease (Symptomatic GERD), Barrett's esophagus, functional dyspepsia including NUD (Non Ulcer Dyspepsia), gastric cancer, stomach MALT lymphoma or hyperacidity; or a suppressant of upper gastrointestinal hemorrhage due to peptic ulcer, acute stress ulcer, hemorrhagic gastritis or invasive stress; and the like. Since compound (I) shows low toxicity and is superior in water-solubility, in vivo kinetics and efficacy expression, it is useful as a pharmaceutical composition. Moreover, since compound (I) is stable even under acidic conditions, it can be administered orally as a conventional tablet and the like without formulating into an enteric-coated preparation. This has an advantageous consequence that the preparation (tablet and the like) can be made smaller, and can be easily swallowed by patients having difficulty in swallowing, particularly the elderly and children. In addition, since it is free of a sustained release effect afforded by enteric-coated preparations, a gastric acid secretion-suppressive action is expressed rapidly, and symptoms such as pain and the like can be alleviated rapidly.

The invention claimed is:

1. A compound represented by the formula

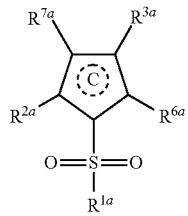

(Ia)

wherein ring C is a saturated or unsaturated 5-membered ring group having 1 to 4 hetero atoms selected from a nitrogen atom, an oxygen atom and a sulfur atom, $R^{1a}$ is an optionally substituted aryl group, an optionally substituted 5- or 6-membered aromatic heterocyclic group or a fused ring group thereof, $R^{2a}$ is an optionally substituted aryl group or an optionally substituted heteroaryl group, $R^{6a}$ and $R^{7a}$ are each absent, or a hydrogen atom, a $C_{1-4}$ alkyl group, a halogen atom or a cyano group, and $R^{3a}$ is an aminomethyl group optionally substituted by 1 or 2 $C_{1-4}$ alkyl groups; wherein the ring-constituting atom of ring C to which substituent $R^{2a}$ is bonded and the ring-constituting atom of ring C to which substituent $R^{3a}$ is bonded are each a carbon atom or a nitrogen atom; excluding a compound represented by the formula

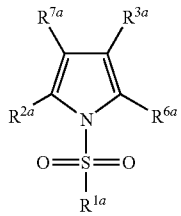

wherein each symbol is as defined above, or a salt thereof.

2. The compound of claim 1, which is represented by the formula (Ia-5)

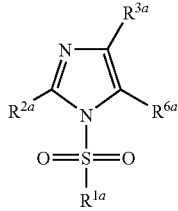

(Ia-5)

wherein $R^{1a}$ is a $C_{6-14}$ aryl group or a 5- or 6-membered aromatic heterocyclic group or a fused ring group thereof, which is optionally substituted by substituent(s) selected from (i) halogen, (ii) hydroxy, (iii) cyano, (iv) $C_{1-6}$ alkyl optionally substituted by halogen, (v) $C_{1-6}$ alkoxy optionally substituted by halogen, (vi) an amino group optionally substituted by $C_{1-6}$ alkyl, (vii) oxo, (viii) carbamoyl, (ix) mono-$C_{1-6}$ alkyl-carbamoyl, (x) di-$C_{1-6}$ alkyl-carbamoyl, (xi) $C_{1-6}$ alkylsulfonyl and (xii) $C_{1-6}$ alkyl-carbonylamino, $R^{2a}$ is an optionally substituted alkyl group, an optionally substituted aryl group or an optionally substituted heteroaryl group, $R^{3a}$ is an aminomethyl group optionally substituted by 1 or 2 $C_{1-4}$ alkyl groups, and $R^{6a}$ is a hydrogen atom, a $C_{1-4}$ alkyl group, a halogen atom or a cyano group.

3. A pharmaceutical composition comprising the compound of claim 1, and a pharmaceutical acceptable carrier.

4. A method of treating peptic ulcer, gastritis, reflux esophagitis, or symptomatic gastroesophageal reflux disease (symptomatic GERD), which comprises administering an effective amount of the compound of claim 1 to a mammal.

* * * * *